US007037533B2

(12) United States Patent
Jung et al.

(10) Patent No.: US 7,037,533 B2
(45) Date of Patent: May 2, 2006

(54) FUNCTIONAL AGENT FOR DECOMPOSING NICOTINE AND METHOD OF PREPARING THE SAME

(75) Inventors: Jong-Moon Jung, 104-1101, Hyundai apt, 700-1, Pongdeokcheon-ri, Suji-eup, 449-756, Yongin-city, Kyungki-do (KR); Ji-Hoon Kim, Taejeon (KR); Eun-Ju Kim, Cheonan (KR); Myoung-Gyu Park, Cheonan (JP)

(73) Assignees: Regen Biotech, Inc., (KR); Jong-Moon Jung, (KR)

( * ) Notice: Subject to any disclaimer, the term of this patent is extended or adjusted under 35 U.S.C. 154(b) by 62 days.

(21) Appl. No.: 10/468,500

(22) PCT Filed: Feb. 21, 2002

(86) PCT No.: PCT/KR02/00280

§ 371 (c)(1),
(2), (4) Date: Aug. 18, 2003

(87) PCT Pub. No.: WO02/065978

PCT Pub. Date: Aug. 29, 2002

(65) Prior Publication Data

US 2004/0096526 A1    May 20, 2004

(30) Foreign Application Priority Data

Feb. 21, 2001    (KR)    ............................ 2001-0008602
Feb. 20, 2002    (KR)    ............................ 2002-0009104

(51) Int. Cl.
*A61K 35/78*    (2006.01)
(52) U.S. Cl. ...................... 424/729; 424/725; 424/736; 424/752; 424/774; 424/776; 424/777
(58) Field of Classification Search ................ 424/725, 424/729, 736, 752, 774, 777, 776
See application file for complete search history.

(56) References Cited

U.S. PATENT DOCUMENTS 5,087,671 A    2/1992    Loeppky et al.

FOREIGN PATENT DOCUMENTS

CN    1161857    * 10/1997
FR    2255081    * 8/1975
KR    010014750    2/2001

OTHER PUBLICATIONS

Damaj, M.I., Welch, s.P. and Martin, B.R. (1996) J. Pharmacol. Exp. Thr., 277 454-461.
Magee, P.N., and Barnes, J.M. (1956) Br. J. Cancer, 10. 114-122.
Druckrey, H., Preussmann, R., Ivankovic, S., and Schmahl, D. (1967) Z. Krebsforsch, 69, 103-201.
Preussmann, R., and Stewart, B.W. (1984) N-nitroso carcinogens. In Chemical Carcinogensis, (Searle, C.E., Ed.) pp. 643-828, American Chemical Society, Washington, D.C.
Bogovski, P., and Bogovski, S. (1981) Int. J. Cancer, 27, 471-474.
Duckrey, H., and Preussmann, R. (1962) Die Naturwissenschaften, 49, 498-499.
Boyland, E., Roe, F.J.C., and Gorrod, J.W. (1964) Nature, 202, 1126.
Boyland, E., Roe, F.J.C., and Gorrod, J.W., and Mitchley, B.C.V. (1964) Br. J. Cancer, 18, 265-270.
Smith, P.A. S., and Loeppky, R.N. (1967) J. Am. Chem. Soc., 89, 1147-1152.
Klus, H., and Khuh, H. (1975) Fachliche Mitteiulungen der Austria Tabakwerke A.G., 16, 307-317.
Hecht, S.S., chen, C.B., Dong, M. , Omaf R.M., Hoffmann, D., and Tso, T.C. (1977) Beitr. Tabakforsch., 9, 1-6.
Hecht, S.S., Chen, C.B., and Hoffmann, D. (1976) Tetrahedron Let., 8, 503-506.
Hecht, S.S., Chen, C.B., Omaf, R.M., Jacobs, E., Adams, J.D., and Hoffmann, D. (1978) J. Org. Chem., 43, 72-76.
Hecht, S. S., Chen, C. B., Dong, M., Omaf, R. M., Hoffmann, D., and Tso, T. C. (1977).
Cashman, J. R., Park, S. B., Yang, Z. C., Wrighton, S. A., Jacob. P. III., and Benowitz, N. L. (1992) *Chem. Res. Toxicol.*, 5,639-646.
Benowitz, N. L., Jacob. P. III., and Fong, I. (1994) *J. Pharmacol. Exp. Ther.*, 268,296 303.
Kyerematen, G. A., Morgan, M. L., Chattopadhyay, B., deBethizy, J. D., and Vesell, E. S. (1990) *Clin. Pharmacol. Ther.*, 48,641-651.
Caldwell, W. S., Greene, J. M., Byrd, G. D., Chang, K. M, Uhrig, M. S., deBethizy, J. D., Crooks, P. A., Bhatti, B. S., and Riggs, R. M. (1992) *Chem. Res. Toxicol.*, 5,280-285.
Byrd, G. D., Chang, K-M., Greene, J. M., deBethizy, J. D. (1992) *Drug, Metab. Dispos.*, 20, 192-197.
Jacob. P. III., Benowitz, N. L., and Shulgin, A. T. (1998) *Pharmacol. Biochem. Behav.*, 30, 249-253.

(Continued)

*Primary Examiner*—Christopher R. Tate
(74) *Attorney, Agent, or Firm*—Blakely Sokoloff Taylor & Zafman

(57)    ABSTRACT

The present invention related to a functional agent for decomposing nicotine and a method of preparing the same. The agent includes natural plant extracts such as green tea leaves, mulberry leaves, ginkgo nuts, celery, lemon, apple, dried orange peel, and licorice root. The functional agent of the present invention facilitates the decomposition of nicotine and inhibits the generation of carcinogen. In addition, the functional agent shows an anti-oxidant effect, inhibits mutation and remarkably reduces the generation rate of lung cancer.

5 Claims, 29 Drawing Sheets

OTHER PUBLICATIONS

Brown, B. G., Ching-jey, G. C, Paul, H. A., Chin, K. L., and David, J. D. (1999) *Toxicol Scien.*, 47, 33-39.

Brunnemann, K. D., et al. (1991) *Crit Rev Toxicol.*, 21(4), 235-40.

Barlow, R. D., Stone, R. B., Wald, N. J., and Puhakainen, E. V. J. (1987) *Clin. Chim. Acta.*, 165,45-52.

Lee DH. (1998) *J. Biochem. Molecular Biology*, 31 (2), 196-200.

Joseph, D., Lajos H., Nigel, H., Stanley, I. R., and Timothy, T. (1992) *J. Chromatogr.*, 579, 93-98.

Yamazaki, H., Inui, Y., Yun, C. H., Guengerich, F. P., and Shimada, T. (1992) *Carcinogenesis*, 13, 1789-1794.

Code, E., Crespi, C., Penman, B., Gonzalez, F., Chang, T., and Waxman, D. (1997) *Drug Metab. Dispos.*, 25,985-993.

Maron, D., Ames, B. N. (1983) Revised methods for the Salmonella mutagenicity test. *Mutation Research*, 113, 173-215.

Palinski, W., Rosenfeld, M. E., Yla, H. S., Gurtner, G. C., Socher, S. S., Butler, S. W., Parthasarathy S, Carew, T. E., Steinberg, D., and Witztum, J. L. (1989) *Proc. Natl. Acad. Sci.*, 86, 1372-1376.

Hammond, B., Kontos, H. A., and Hess, M. L. (1985) *Can J. Physiol. Pharmacol.*, 63, 173-187.

Cheeseman, K. H., and Forni, L. G. (1988) *Biochem. Pharmacol.*, 37,4225-4233 Weitzman, S. A., Weitberg, A. B., Clark, E. P., and Stossel, T. P. (1985) *Science*, 227, 1231-1233.

Weitzman, S. A., Weitberg, A. B., Clark, E. P., and Stossel, T. P. (1985) *Science*, 227, 1231-1233.

Fantone, J. C., and Ward, P. A. (1985) *Human Pathol.*, 16,973-978.

Yoshida, M., Sakai, T., Hosokawa, N., Marui, N., Matsumoto, K., Fujioka, A., Nishino, H., Aoike, A. (1990) *FEBS Lett.* 15;260(1):10-3.

Agullo, G., Gamet, L., Besson, C., Demigne, C., Remesy, C. (1994) *Cancer Lett.* 25;87(1):55-63.

Hoffmann, D., Rivenson, A., Chung, F-L., and Hecht, S. S. (1991) *Crit. Rev. Toxicol.*, 21, 305-311.

Wang, Z. Y., Hong, J. Y., Huang, M. T., Reuhl, K. R., Conney, A. H., and Yang, C. S. (1992) *Cancer Res.* 52, 1943-1947.

Xu, Y., Ho, C-T., Amin, S. G., Han, C., and Chung, F-L. (1992) *Cancer Res.* 52, 3875-3879.

Chung, F-L., Wang, M., Rivenson, A., Iatropoulos, M. J., Reinhardt, J. C., Pittman, B., Ho, C. T., and Amin, S. G. (1998) *CancerRes.* 58,4096-4101.

CN 1176749 A (Liu S) Mar. 25, 1998 (ABSTRACT).

CN 1100322 A (Song X) Mar. 22, 1995 (ABSTRACT).

CN 1116053 A (Tan R) Feb. 7, 1996 (ABSTRACT).

CN 1084018 A (Dong Fang Medical Treatment & Health Care) Mar. 23, 1994 (ABSTRACT).

CN 1242210 A (Chenggong Patent Tech Res Inst Wuhao Cit) Jan. 26, 2000 (ABSTRACT).

Ferry, D. R., Smith, A., Malkhandi, J., Fyfe, D. W., deTakats, P. G., Anderson, D., Baker, J., Kerr, D. J. (1996) *Cancer Res*, 2(4):659-68.

Scambia, G., Ranelletti, F. 0., Benedetti, Panici, P., Piantelli, M., Bonanno, G., De Vincenzo, R., Ferrandina, G., Pierelli, L., Capelli, A., Mancuso, S. (1991) *Cancer Chemother Pharmacol.* 28(4): 255-8.

Larocca, L. M., Piantelli, M., Leone, G., Sica, S., Teofili, L., Panici, P. B., Scambia, G., Mancuso, S., Capelli, A., Ranelletti, F. 0. (1990) Type II oestrogen binding sites in acute lymphoid and myeloid leukaemias: growth inhibitory effect of oestrogen and flavonoids. *Br J Haematol.* 75(4):489-95.

Scambia, G., Ranelletti, F. 0., Benedetti, Panici, P., Bonanno, G., De Vincenzo, R., Piantelli, M., Mancuso, S. (1990) Synergistic antiproliferative activity of quercetin and cisplatin on ovarian cancer cell growth. *Anticancer Drugs.* 1 (1):45-8.

Altern. Med Rev. 1999 "Green tea (*Camellia sinensis*) extract and its possible role in the prevention of cancer", Brown MD; NCBI.

J. Korean Soc Food Sci. Nutr., "Effects of Water-Soluble Extract from Leaves of *Morus alba* and *Cudrania tricuspidata* on the Lipid Peroxidation in Tissus of Rats", 6 pages.

Free Radical Res. 1999, "The polyphenolic content of fruit and vegetables and their antioxidant activities. What does a serving constitute", NCBI, Paganga et al.

Yao Xue Xue Bao. 1989:24 "Effects of glycyrrhiza flavonoid on lipid peroxidationand active oxygen radicals", Ju et al.,m NCBI.

Phytother Res. 1999; "Additional information to the in vitro antixoidant activity of Ginkgo biloba L.", Lugas et al, NCBI.

Chem Pharm Bull Jul. 1992; Studies on natural antioxdants in citrus species 1. Determination of antioxidative activities of citrus fruits' Tanizawa, et al., NCBI.

\* cited by examiner

FUNCTIONAL AGENT FOR DECOMPOSING NICOTINE AND METHOD OF PREPARING THE SAME

The present patent application is a non-provisional application of International Application No. PCT/KR02/00280, filed Feb. 21, 2002.

BACKGROUND OF THE INVENTION (a) Field of the Invention

The present invention relates to a functional agent for decomposing nicotine and method of preparing the same, and more specifically a functional agent that removes the harmfulness of nicotine caused by smoking and can inhibit the generation of carcinogen caused by smoking.

(b) Description of the Related Art

Nicotine is colorless or a light yellow poisonous liquid that is absorbed into a body by smoking. Nicotine is so poisonous that it affects the cellular membrane of nerve ganglion. In addition, nicotine is known as causing an increase in blood pressure, convulsion of skeletal muscle fiber, and mouth paralysis due to excitation.

Instant harmfulness of nicotine includes contraction of the pupil, eye sight opacity, vomit, nausea, stomach ache, diarrhea, difficulty in controlling urination, laryngeal burn, difficulty in breathing, increase of secretion in salvia and a respiratory organ, blue disease, and decrease of pulse beat. When smoking is prolonged, nicotine is accumulated in a body so that it can cause cancer, hypertension, mouth disease, various gastrointestinal disorders due to excessive acid dyspepsia, and various circulatory diseases such as arteriosclerosis. Also, nicotine is an important factor in facilitating aging and in severe cases, it causes spasms, convulsion, breathing paralysis, muscle convulsion, and unnecessary hypertension (Damaj, M. I., Welch, S. P. and Martin, B. R. (1996) *J. Pharmacol. Exp. Thr.*, 277 454–461).

Nicotine acts as a very strong carcinogen by nicotine-derived nitrosamine. There are hundreds of million of patients suffering from lung cancer and lung diseases caused by smoking all over the world every year. In 1956, Magee and Barnes proved that N'-nitrosodimethyl amine (NDMA) is a very strong liver cancer-inducing material in rats (Magee, P. N., and Barnes, J. M. (1956) *Br. J. Cancer*, 10. 114–122) and thereafter over 30 species of N-nitrosamine compounds are confirmed as having carcinogen-activity (Druckrey, H., Preussmann, R., Ivankovic, S., and Schmahl, D. (1967) *Z. Krebsforsch.*, 69, 103–201 ; Preussmann, R., and Stewart, B. W. (1984) N-nitroso carcinogens. *In Chemical Carcinogenesis,* (Searle, C. E., Ed.) pp 643–828, American Chemical Society, Washington, DC. ; Lijinsky, W. (1992) *Chemistry and Biology of N-Nitroso Compounds*, Cambridge University Press, Cambridge, England.; Bogovski, P., and Bogovski, S. (1981) *Int. J. Cancer*, 27, 471–474).

In 1962, Druckrey and Preussmann suggested that nitrosamine which was derived from alkaloid of tobacco existed in tobacco smoke(Druckrey, H., and Preussmann, R. (1962) *Die Natur.*, 49, 488–499). In 1964, Boyland et al confirmed that NNN(N'-nitrosonornicotine) occurs a lung cancer in mouse and NAB(N'-nitrosoanabasine) occurs cancer of the esophagus in rats (Boyland, E., Roe, F. J. C., and Gorrod, J. W. (1964) *Nature*, 202, 1126; Boyland, E., Roe, F. J. C., and Gorrod, J. W., and Mitchley, B. C. V. (1964) *Br. J. Cancer*, 18, 265–270).

Smith et al proved that various nitrosamine is generated from nicotine in his classical research (Smith, P. A. S., and Loeppky, R. N. (1967) *J. Am. Chem. Soc.*, 89, 1148–1152) based on nitrosation of tertiary amine via iminium ion (Klus, H., and Kuhn, H. (1975) *Fachliche MittAustria Tabakwerke*, 16, 307–317; Hecht, S. S., Chen, C. B., Dong, M., Ornaf, R. M., Hoffmann, D., and Tso, T. C. (1977) *Beitr. Tabakforsch.*, 9, 1–6). Hecht et al confirmed that 4-(methylnitrosamino)-1-(3-pyridyl)-1-1-butanone (NNK), 4-(methylnitrosamino)-4-(3-pyridyl)-butanal(NNA), NNN and other nitro compounds are generated from nicotine and detected NNK from tobacco (Hecht, S. S., Chen, C. B., and Hoffmann, D. (1976) *Tetrahedron Lett.*, 8, 593–596; Hecht, S. S., Chen, C. B., Ornaf, R. M., Jacobs, E., Adams, J. D., and Hoffmann, D. (1978) *J. Org. Chem.*, 43, 72–76; Hecht, S. S., Chen, C. B., Hirota, N., Ornaf, R. M., Tso, T. C., and Hoffmann, D. (1978) *J. Natl. Cancer Inst.*, 60, 819–824).

FIG. 1 shows various nitrosamines metabolized from nicotine.

Until now, seven tobacco-specific nitrosamines such as NNN, NNK, NNAL, NAT, NAB, iso-NNAN and iso-NNAC were identified from products of tobacco and NNN, NNK, and NAT were detected in larger amount than others. Particularly, NNN, NNK, and NNAL have already been confirmed as very strong carcinogens.

Nicotine is metabolized to cotinine through two processes and cytochrome $P_{450}$ (hereinafter, CYP) and cytosol aldehyde oxygenase are involved on the metabolism. Nicotine is metabolized to cotinine by various CYPs, and CYP 2A6 has an important role (Cashman, J. R., Park, S. B., Yang, Z. C., Wrighton, S. A., Jacob. P. III., and Benowitz, N. L. (1992) *Chem. Res. Toxicol.*, 5, 639–646).

FIG. 2 shows the metabolism of nicotine to cotinine.

70 to 80% of nicotine is conversed into cotinine and 10 to 15% of cotinine is excreted as urine and the remainder is metabolized to ketoic acid. 85% of ketoic acid is metabolized to hydroxy acid and excreted as urine. 4% of nicotine that is not metabolized to cotinine is conversed into nicotine-1-N-oxide by FMO (flavin-containing monooxygenase) and most is excreted as urine (Benowitz, N. L., Jacob. P. III., and Fong, I. (1994) *J. Pharmacol. Exp. Ther.*, 268, 296–301). Therefore, 80 to 90% of nicotine is excreted as urine through metabolism (Kyerematen, G. A., Morgan, M. L., Chattopadhyay, B., deBethizy, J. D., and Vessel, E. S. (1990) *Clin. Pharmacol. Ther.*, 48, 641–651; Caldwell, W. S., Greene, J. M., Byrd, G. D., Chang, K-M, Uhrig, M. S., deBethizy, J. D., Crooks, P. A., Bhatti, B. S., and Riggs, R. M. (1992) *Chem. Res. Toxicol.*, 5, 280–285 ; Byrd, G. D., Chang, K-M., Greene, J. M., deBethizy, J. D. (1992) *Drug. Metab. Dispos.*, 20, 192–197 ; Jacob. P. III., Benowitz, N. L., and Shulgin, A. J. (1988) *Pharmacol. Biochem. Behav.*, 30, 249–253).

As shown in FIG. 3, NNK is a pro-carcinogen to laboratory animals and is mainly metabolized in the liver and the lung by CYP enzyme. The main step of NNK activation is α-hydroxylation mediated by CYP and in the reaction, NNK converts to methyl-diazohydroxide which is an unstable metabolite and it gives methyl group to DNA and generates $O^6MeG$. $O^6MeG$ has been used as a promutagenic biological index for carcinogen derived from NNK.

It was reported that CYP is related to α-hydroxylation of NNK and NNN in A/J mouse, induces methylation of DNA, and forms $O^6$-methylguanine($O^6MeG$) so that GC->AT transitional mispairing occurs and it activates K-ras proto-oncogene (Brown, B. G., Ching-jey, G. C, Paul, H. A., Chin, K. L., and David, J. D. (1999) *Toxicol Scien.*, 47, 33–39).

Therefore, it was suggested that lung cancer caused by NNK through CYP could be effectively inhibited by using a substrate competitive inhibitor against substrate of CYP enzyme such as nicotine or cotinine in vitro or in vivo because it inhibits the activation of NNK metabolism(α-hydroxylation)(Brunnemann, K. D., et al. (1991) *Crit Rev Toxicol.*, 21(4), 235–40). FIG. 4 shows structural similarity between NNN, nicotine, and NNK that are related to the metabolism of cytochrome $P_{450}$ 2A6.

Cotinine that is a main metabolite of nicotine, and ketoic acid and hydroxyl acid that are metabolite thereafter, are rapidly metabolized and excreted as urine. This metabolism has variation according to people. Cotinine, ketoic acid and hydroxyl acid are only factors affected by smoking, not a carcinogen. Furthermore, they act as competitive inhibitors to inhibit tobacco-specific nitrosamine converting carcinogen through CYP existing in the liver. Therefore, nicotine that is rapidly metabolized to cotinine, can reduce the harmfulness of smoking and inhibit cancer more effectively than nicotine that converts to derivatives such as NNK, NNA and NNN.

SUMMARY OF THE INVENTION

It is an object of the present invention to provide a functional agent for rapidly decomposing harmful chemicals caused by smoking.

It is another object of the present invention to provide a functional agent that can inhibit the generation of carcinogen such as nicotine and nicotine derivatives.

In order to accomplish the objects, the present invention provides a functional agent for decomposing nicotine prepared by drying a composition comprising:

(a) 50 to 500 parts by weight of powder of green tea efficient ingredient extracted from green tea leaves;

(b) 7.5 to 75 parts by weight of mulberry leaves extract steeped from boiling water;

(c) 3 to 30 parts by weight of apple juice;

(d) 3 to 30 parts by weight of licorice root extract steeped from boiling water; and (e) 1.5 to 15 parts by weight of dried orange peel extract steeped from boiling water.

The present invention also provides a functional drink for decomposing nicotine prepared by mixing 0.1 to 5% by weight of the functional agent with water.

The present invention also provides a method of preparing a functional agent comprising:

(a) preparing fruit and vegetable filtrates by extracting and filtering ginkgo nut, celery, apple and lemon;

(b) preparing leaves and herbs concentrates by extracting licorice root and dried orange peel at 100° C., mixing mulberry leaves and extracting and filtering them; and (c) preparing powder by mixing fruit and vegetable filtrates of (a), leaves and herbs concentrates of (b) and green tea powder, filtering and spray-drying them.

DETAILED DESCRIPTION AND THE PREFERRED EMBODIMENTS

Figure 1:
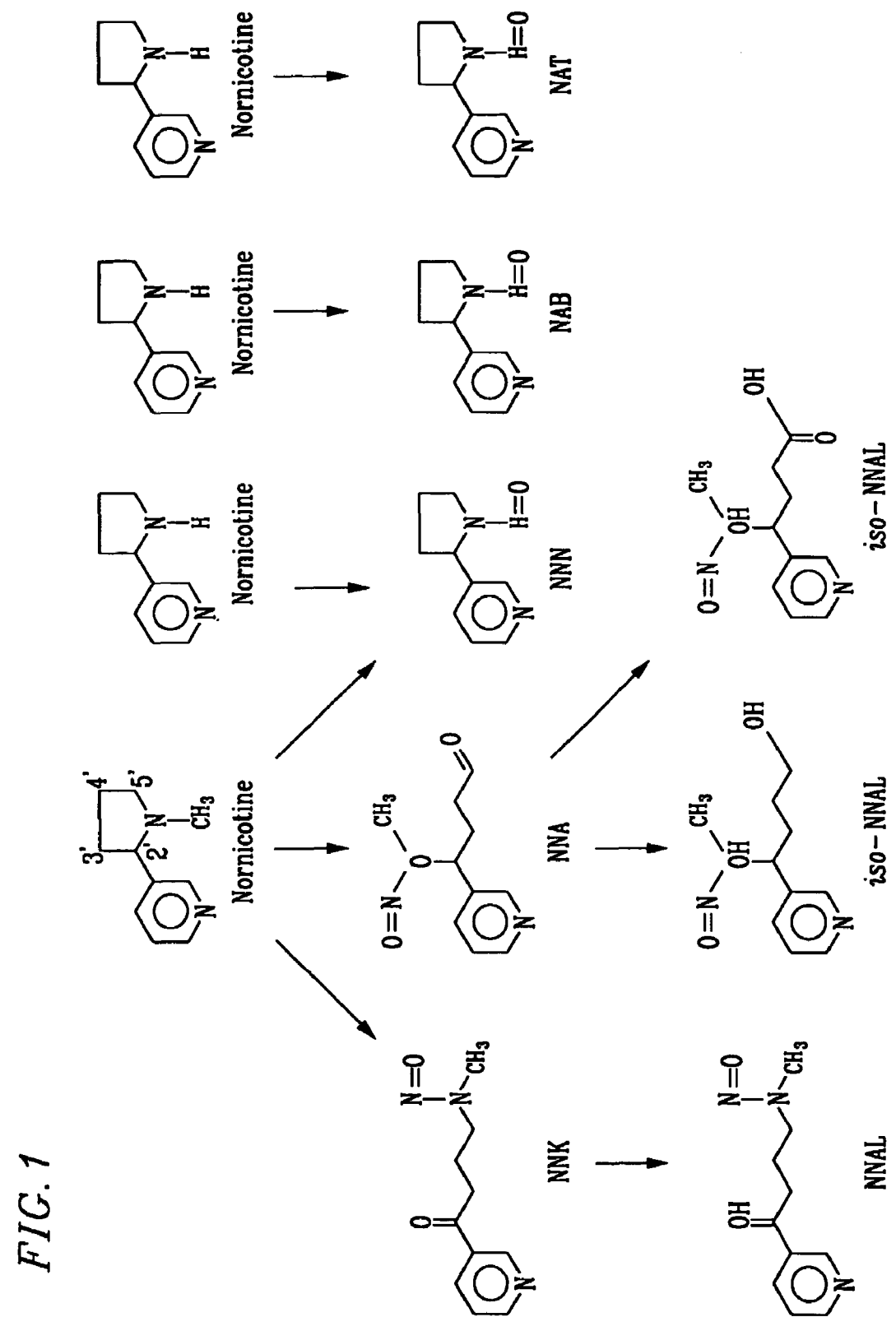
FIG. 1 shows nitrosamine generated from nicotine.
Figure 2:
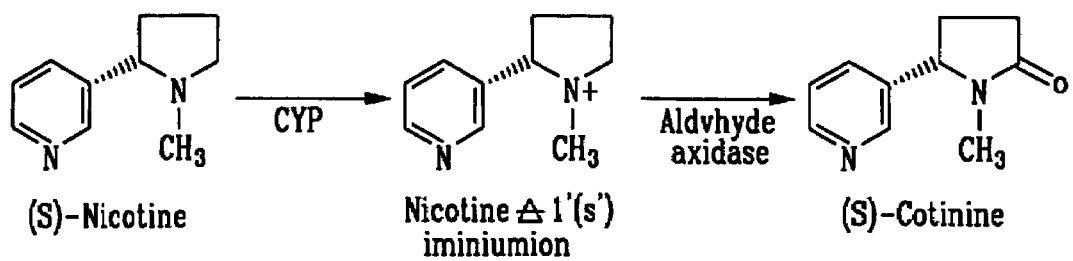
FIG. 2 shows metabolism of nicotine into cotinine.
Figure 3:
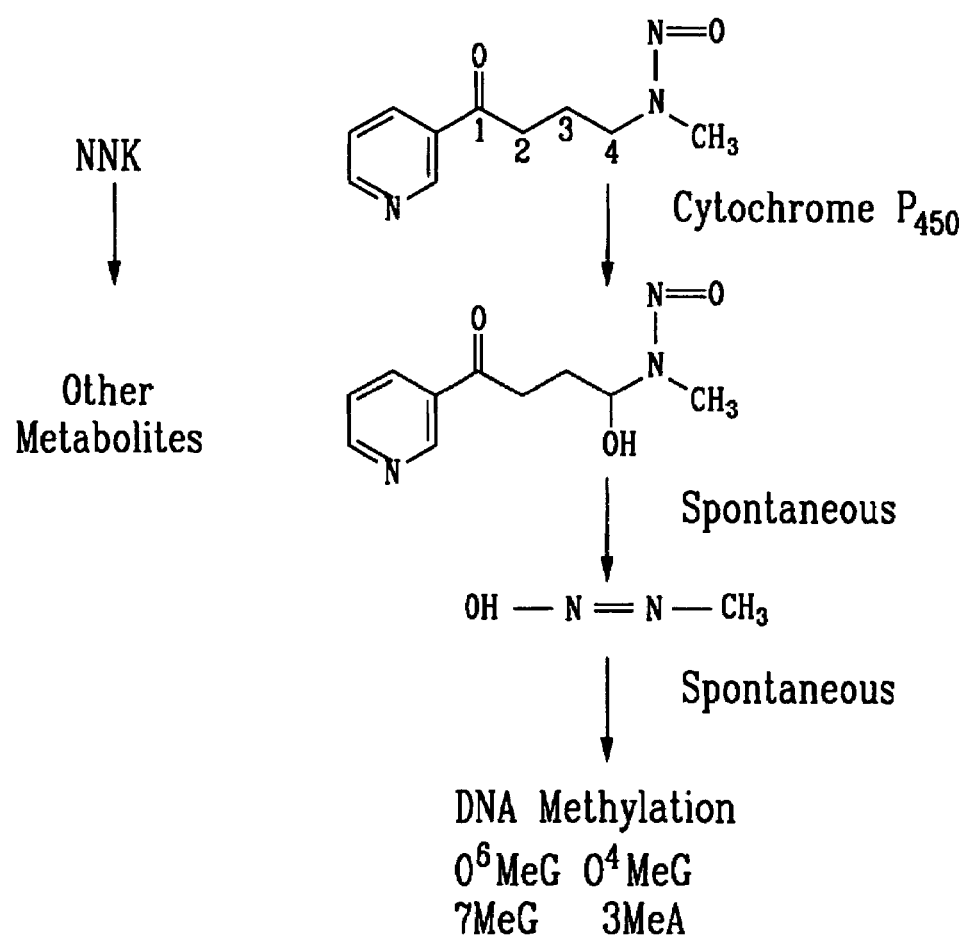
FIG. 3 shows the metabolic mechanism of 4-(methylnitrosamino)-1-(3-pyridyl)-1-butanone (NNK).
Figure 4:
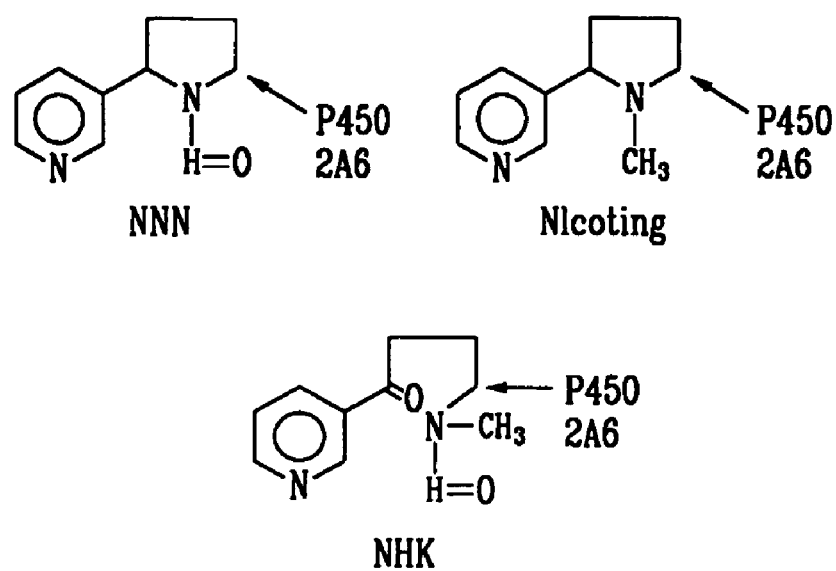
FIG. 4 shows the structural similarity between NNN (N'-nitrosonor nicotine), nicotine, and NNK that are related to metabolism of cytochrome $P_{450}$ 2A6.

During research to improve the decomposability of nicotine in a body, the present inventors studied that when the natural food is added to green tea containing a lot of catechin and EGCG, and apple extract containing quercetin, it becomes an excellent functional agent to decompose and inhibit to generate a harmful ingredient of tobacco.

The functional agent for decomposing nicotine of the present invention is prepared by drying a composition comprising (a) 50 to 500 parts by weight of powder of green tea efficient ingredient extracted from green tea leaves; (b)

7.5 to 75 parts by weight of mulberry leaves extract steeped from boiling water; (c) 3 to 30 parts by weight of apple juice; (d) 3 to 30 parts by weight of licorice root extract steeped from boiling water; and (e) 1.5 to 15 parts by weight of dried orange peel extract steeped from boiling water.

The functional agent of the present invention further contains extracts prepared by drying a composition comprising (a) 7.5 to 75 parts by weight of ginkgo nut extract; (b) 3 to 30 parts by weight of celery extract; and (c) 3 to 30 parts by weight of lemon extract.

The functional agent for decomposing nicotine of the present invention comprises preferably (a) 100 to 200 parts by weight of powder of green tea efficient ingredient extracted from green tea leaves; (b) 15 to 30 parts by weight of mulberry leaves; (c) 15 to 30 parts by weight of ginkgo nut; (d) 6 to 12 parts by weight of celery; (e) 6 to 12 parts by weight of lemon; (0 6 to 12 parts by weight of apple; (g) 6 to 12 parts by weight of licorice root; and (h) 3 to 6 parts by weight of dried orange peel.

The drying method of the functional agent for decomposing nicotine of the present invention can be conventional drying methods, preferably a spray-drying method.

The functional agent may be used by itself or included with more than one pharmaceutical composition. A composition comprising the functional agent can include more than one kind of pharmaceutical diluent, selected from the group consisting of saline, buffered saline, dextrose, water, glycerol, and ethanol, but the diluent is not limited. Appropriate diluents are listed in the written text of Remington's Pharmaceutical Science (Mack Publishing co, Easton Pa.).

The functional agent or the composition comprising functional agent can be administered via oral or parenteral routes. Parenteral dosing means the administration of a drug through a route other than oral, which includes rectal, intravenous, intraperitoneal and intramuscular, intra-arterial, transdermal, nasal, inhalation, ocular, and subcutaneous introduction.

Pharmaceutical formulations containing the functional agent may be prepared in any form, such as oral dosage form, injectable solution, or topical preparation. The examples of pharmaceutical formulation are follow: plasters, granules, lotions, liniments, lemonades, aromatic waters, powders, syrups, ophtalmic ointments, liquids and solutions, aerosols, extracts, elixirs, ointments, fluid extracts, emulsions, suspesions, decoctions, infusions, tablets, suppositiories, injections, spirits, cataplsma, capsules, creams, troches, tinctures, pastes and pills.

The formulation can be preferably prepared for oral and injectable administration and most preferably in oral form such as tablet, capsule, soft capsule, aqueous medicine, pill, granule, and the like.

In preparing the formulation, the functional agent are filled in the soft capsule without any excipient, or formed as an appropriate formulation after mixing or diluting with a carrier. Examples of suitable carriers are starches, water, saline, Ringer's solution, dextrose, and any ingredients described in previous reports (e.g. Remington's Pharmaceutical Science, Mack Publishing Co., Easton Pa.).

The functional agent for decomposing nicotine of the present invention can be used as drinks for heath or food additives, and preferably food, food additives, medicines, drinks, or drink additives. It is also preferable to mix 0.1 to 5% by weight of the functional agent with water to prepare a functional drink.

The functional agent or drink for decomposing nicotine of the present invention facilitates decomposition of nicotine and inhibits generation of nitroso-compound that is carcinogen. Also, the functional agent inhibits cytochrome $P_{450}$ 1A2 enzyme activity so that it prevents the formation of carcinogen by NNK. In addition, it shows an anti-oxidation effect as well as it inhibits mutagenicity by NNK and benzopyrene and it reduces the gene ration rate of lung cancer.

The functional agent for decomposing nicotine of the present invention comprises about 0.32 mg/mg of catechin and 56 ng/mg of quercetin.

The functional agent is prepared by filtrating fruit and vegetable, concentrating leaves and herbs, and mixing and drying that.

The fruit and vegetable filtrates is prepared by washing, grinding, extracting and filtering 7.5 to 75 parts by weight of ginkgo nuts, 3 to 30 parts by weight of celery, 3 to 30 parts by weight of lemon, and 3 to 30 parts by weight of apple. Filtration can be a conventional method, and more preferably mesh or diatomite is used. It is most preferable to filter by using 100 meshes net and diatomite to prevent precipitation in an aqueous phase. Also, in the filtration step, it is preferable to add a moderate amount of water into the sludge after first extraction and stir, extract and filter again in order to effectively extract efficient ingredients. The fruit and vegetable filtrates are stored at 0 to 7° C.

The leaves and herbs concentrates are prepared by adding 400 to 4000 parts by weight of water, 3 to 30 parts by weight of licorice root, and 1.5 to 15 parts by weight of dried orange peel into an extracting bath, elevating the temperature to 100° C. and extracting them. And then, after adding 100 to 1000 part by weight of water into the extracting bath, 7.5 to 75 parts by weight of mulberry leaves are added. The extracting is preformed for 10 to 40 minutes under 60 to 95° C. The leaves and herbs concentrates are prepared by filtering and concentrating the extract. The above filtering method is preferably a conventional method and more preferably, mesh, housing filtration or diatomite can be used. The most preferable method is filtration with 100 meshes net, 1 μm housing filter and diatomite. After the first extract, 400 to 4000 parts by weight of water is further added to the remaining sludge, and the leaves and herbs concentrates by extracting and filtering them again can be prepared.

The mixing and powder preparation step comprises mixing 50 to 500 parts by weight of powder of green tea efficient ingredient extracted from green tea leaves with the above fruit and vegetable filtrates and the leaves and herbs concentrates, removing precipitation by a high-speed centrifugal separator and drying. Drying can be a conventional method, preferably spray drying.

The present invention is further explained in more detail with reference to the following examples. These examples, however, should not in any sense be interpreted as limiting the scope of the present invention.

EXAMPLE 1

Functional Agent for Decomposing Nicotine

A Preparing Step of Fruit and Vegetable Filtrates 60 kg of peeled and not dried ginkgo nuts, 24 kg of washed celery, 24 kg of apples, and 24 kg of lemons we re squeezed after grinding in a grinder. 100 L of water was added into the sludge after squeeze, stirred for 30 minutes, squeezed again and combined with the first squeezed liquid. The squeezed liquid was filtered through a 100 mesh net and diatomite and stored at 4° C.

A Preparing Step of Leaves and Herbs Concentrates

After adding 0.5 ton of water into a 1.5-ton tank, 24 kg of licorice root and 12 kg of dried orange peel were added and extracted for 2 hours at 100° C. After adding 0.2 ton of water thereto, 60 kg of mulberry leaves were added and firstly extracted for 30 minutes at 80° C. While storing the first extract separately, 0.5 ton of water was added into the sludge and secondly extracted for 30 minutes at 80° C. The first and second extract were mixed, filtered through a 100 mesh net, 1 μm housing filter and diatomite, and concentrated.

A Step of Mixing and Spray Drying

After evenly mixing 100 kg of powder of green tea efficient ingredient extracted from green tea leaves with the fruit and vegetable filtrates and the leaves and herbs concentrates, and removing precipitation by a high-speed centrifugal separator, a nicotine-decomposing agent was prepared by spray drying.

EXAMPLE 2

Functional Drink for Decomposing Nicotine

The functional drink for decomposing nicotine was prepared by mixing 100 ml of water with 0.1 to 5 g of the functional agent for decomposing nicotine of Example 1.

EXAMPLE 3

Test of Effect of the Functional Agent for Decomposing Nicotine

In order to confirm whether material decomposable nicotine exists in the functional agent prepared in Example 1, nicotine decomposability was measured by directly mixing nicotine into water and the functional agent for decomposing nicotine respectively. Water was control.

200 μl of 1 mM nicotine (catalog number N3876, Sigma) and 200 μl of the functional agent solution(0.3%) were evenly mixed in an Eppendorf tube(1.5 ml). After 0, 10, 20, 30, 60, and 120 minutes, an amount of generated cotinine was quantified by a cotinine quantitative method and was shown in FIG. 5. The test temperature was 25° C.

The present test used the modified Barlow method which is simple and more accurate and developed in 1987 (Barlow, R. D., Stone, R. B., Wald, N. J., and Puhakainen, E. J. (1987) *Clin. Chim. Acta.*, 165, 45–52). The specific method is follows.

200 μl of sample and standard were added into buffer solution or distilled water in a 1.5 ml of polypropylene tube. In order to improve the reliability of the test result, three tubes were used per sample. 100 μl of 4M sodium acetate buffer solution(pH 4.7), 40 μl of 1.5M KCN, 40 μl of 0.4M chloramine-T, 200 μl of 78 mM barbituric acid dissolved in 50% by volume of acetonitrile were added in turn into the sample and mixed for 10 seconds. The mixture was reacted for 15 minutes at room temperature (25° C.) and the reaction was stopped after adding 40 μl of 1M sodium metabisulphite. Absorbance was measured at 490 nm and the sample was quantified in comparison with standard cotinine.

Also, the same test was carried out at 15 and 37° C. The reason for the different temperature test is to inspect whether the process related to the generation of cotinine is a chemical reaction or a biological catalyst (such as an enzyme)-related reaction. The result of the different temperature test was almost the same to that of the test at 25° C.

Figure 5:
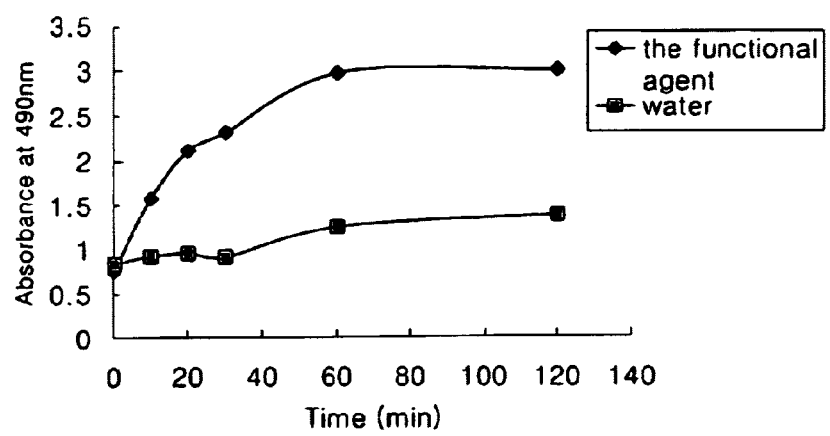
FIG. 5 is a graph showing the nicotine decomposability of the functional agent of the present invention by a direct mixing method.

As shown in FIG. 5, while cotinine absorbance of the functional agent of the present invention was 3.0, absorbance of water was only 1.3. Thus, it is confirmed that there is a nicotine decomposing material in the functional agent of the present invention. In addition, when there was no functional agent, transition time from nicotine to the decomposed product was very slow (about 10 to 20 minutes). On the contrary, it was observed that under the functional agent, cotinine was remarkably generated. This shows that the functional agent of the present invention reacts with nicotine in a test tube so that it facilitates the decomposition of nicotine.

EXAMPLE 4

Measurement of Nicotine Decomposability in Cell Culture

Nicotine and the functional agent were treated to cell, and amount of cotinine generated from nicotine are quantified. Generally, the smoking amount is measured by the amount of nicotine, cotinine, thiocyanate, and carboxyhemoglobin of a smoker. However, since nicotine has a half period of 30 minutes, it is unstable than cotinine which has a half period of 24 hours.

Stock cells were prepared by culturing human hepatocyte derived FLCFR5 cells derived for a week and dividing them into a small amount. In order to quantify, the divided hepatocyte cells were cultured for a week until 100% of confluence. And then, they were further cultured in medium containing nicotine (5% FBS added DMEM (Dulbecco's modified eagle medium), 1 mM nicotine) for a week. 120 μl of the functional agent solution (0.3%) was added into the cultured cells and cultured, and then the cells were collected after 10, 20, 30, 60, 120 minutes. The collected cells were washed three or four times by phosphate buffered saline (PBS) and collected by a scraper. After collecting cells by a centrifugal separator and adding 100 μl of PBS (4° C.), the cells were grinded by an ultra-sonicator (Vibra Cell-200; Newton, Conn., USA) for 30 seconds intermittently and absorbance was measured at 490 nm by DBA method. Also, water was used as control and tested by the same method.

Figure 6:
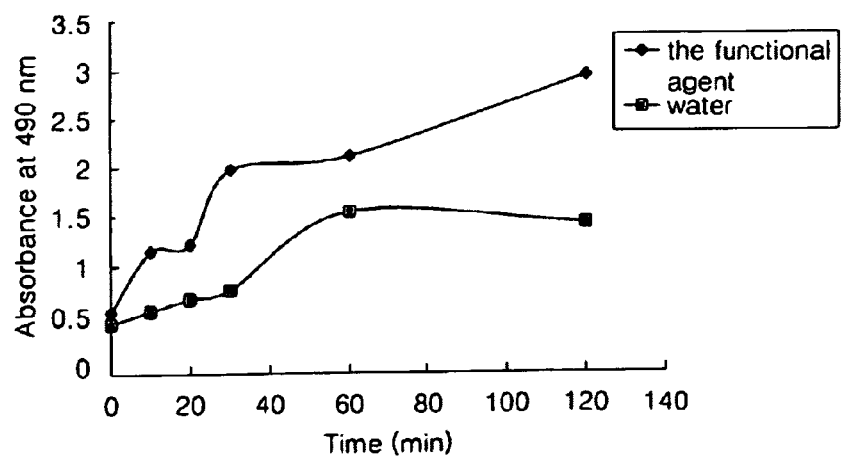
FIG. 6 is a graph showing the nicotine decomposability of the functional agent of the present invention by measuring using FLCFR5 cell strain.

FIG. 6 is a graph showing the nicotine decomposability of the functional agent and it shows that the cells applied by the present functional agent produced more cotinine than control.

In addition, when the functional agent for decomposing nicotine has already absorbed in a cell, the decomposability of newly inserted nicotine are confirmed.

FLCFR5 cells were pre-cultured in a culture medium containing the functional agent (120 μl of the functional agent per 1 ml of medium culture) for 6 hours. After pre-culture, the cells were washed by phosphate buffered saline (PBS) and cultured in a medium containing nicotine. An amount of cotinine in cells was measured by the same method.

Figure 7:
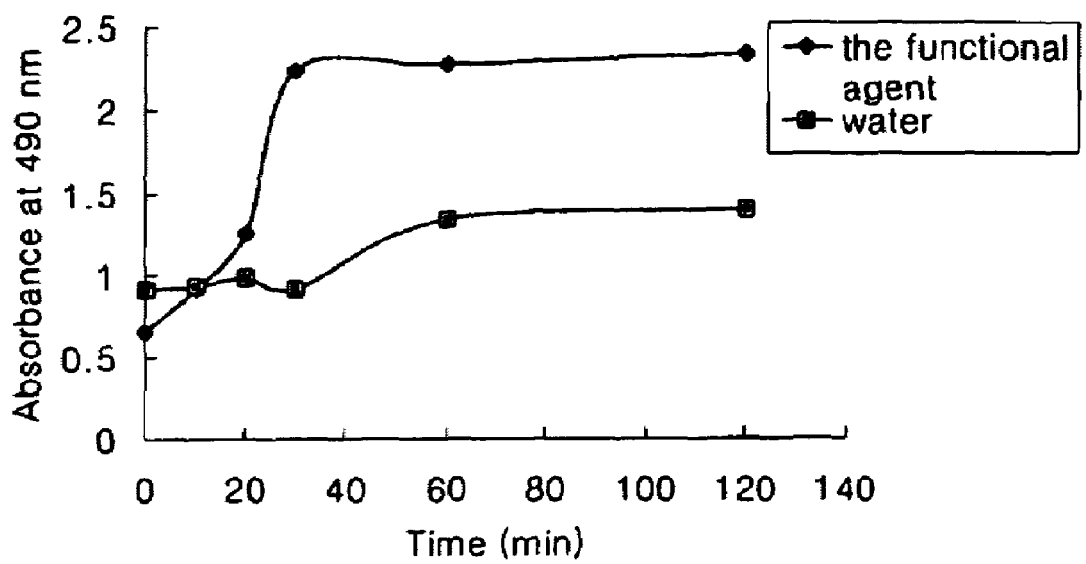
FIG. 7 is a graph showing the nicotine decomposability of the functional agent of the present invention in the cells already absorbed the functional agent.

FIG. 7 shows the nicotine decomposability of the functional agent in the cells that have already absorbed the functional agent. The cells already absorbed the functional agent generated much more cotinine than the cells not absorbed the agent. When comparing with the cells of FIG. 6 wherein the functional agent was added after, the amount of generated cotinine in both cases was similar. This means that there is no remarkable difference between long-term intake of the functional agent and intake just before smoking.

The results of nicotine decomposition in FIGS. 6 and 7 have the same pattern as in FIG. 5 of a direct mixing method. This can be interpreted as follows. An ingredient having nicotine decomposability easily transmits a cell membrane and maintains stability in the cell. The material stability has the same pattern irrespective of cell age. When cells divided identically into complete confluence state were further cultured, the same pattern was observed that they reached 60–100% of confluence. The decomposition of nicotine is remarkably facilitated when there is a functional agent. A common idea that for a smoker who drinks green tea, facilitation of nicotine decomposition and cotinine generation by the functional agen, are due to supplements of vitamin C and nicotine absorption by catechin is inconsistent. This is because accelerated transition from nicotine to cotinine in the presence of green tea extract cannot be explained by the reasons. Thus, we can suggest other assumptions: an unknown ingredient of the functional agent is related to the transition or the transition from nicotine to cotinine is facilitated by a totally different mechanism. A precipitation theory, wherein the catechin precipitates toxic material such as nicotine by absorption, can explain the reduction of free nicotine in a cell. However, it was observed that under the presence of the functional agent, when the cultural time increases, the amount of cotinine increases. This means that an unknown ingredient of the functional agent other than catechin affects the decomposition of nicotine.

EXAMPLE 5

Measurement of Nicotine Decomposability by Using Zenopus Immature Egg

In order to exclude a time gap between the time injected nicotine or the functional agent and the time absorbed into cells, nicotine or the functional agent was directly injected into zenopus immature egg (oocyte) and nicotine decomposability was measured.

After separating the immature egg from the mother and selecting step IV or V which has 1.0 to 1.2 mm of diameter, the egg was cultured for a day at 15° C. in OR2 solution (Byrd, G. D., Chang, K -M., Greene, J. M., deBethizy, J. D. (1992) *Drug. Metab. Dispos.*, 20, 192–197). After cultivation, a protective membrane of the immature egg was directly removed by forcep (watchmaker) before using, and the preparation of multiple immature eggs by removing the protective membranes was carried out by using collagenase type III (Sigma) (Lee D H. (1998) *J. Biochem. Molecular Biology*, 31(2), 196–200).

500 nl of mixing solution of 1 mM of nicotine and 120 µl of the functional agent solution (0.3%) was injected into the immature egg by a micro operator. After injection, the immature eggs were cultured at 15° C., 25° C. (normal temperature), and 32° C. respectively, collected at 0, 10, 20, 30, 60, 120 seconds and carried out homogenizing (dounce homogenizer) in OR2 solution. The yolk of the homogenate was removed by a centrifugal separation and a supernatant solution was taken to quantify cotinine. In addition, in order to exclude the effect of the injection method, nicotine decomposability of the functional agent was confirmed under the concentration of nicotine and the functional agent used in the cell culture test for the same cultural time in OR2 medium culture.

Figure 8:
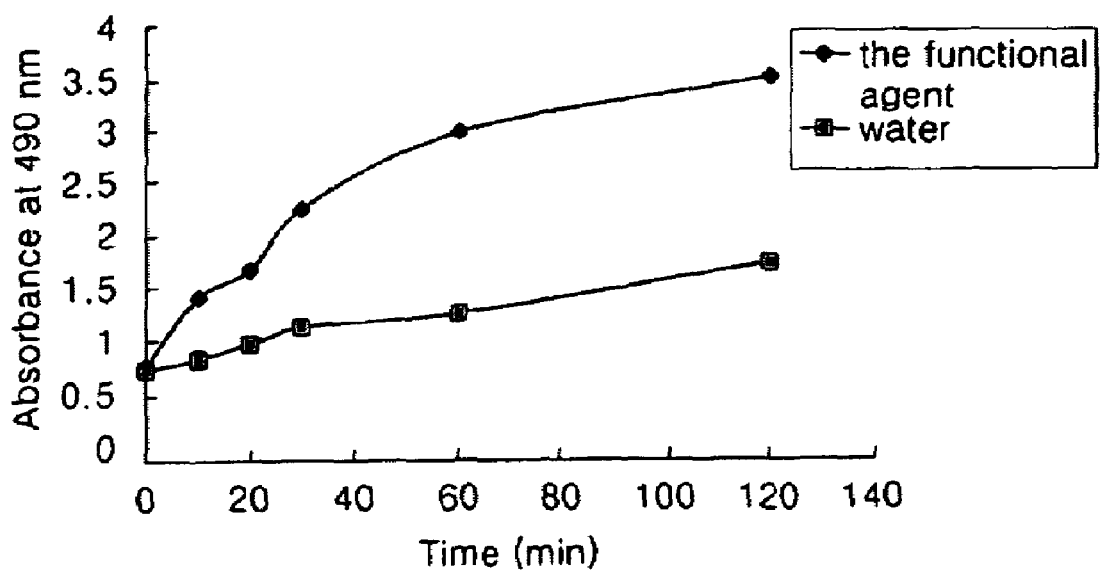
FIG. 8 is a graph showing the nicotine decomposability of the functional agent of the present invention when the functional agent and nicotine is injected together in *zenopus oocyte*.

FIG. 8 is a graph showing nicotine decomposability of the functional agent of the present invention when the functional agent and nicotine is injected in zenopus oocyte. It shows higher nicotine decomposability than that of FIG. 6. Also, the reactivity of the zenopus oocyte was measured according to cultural temperature, but there is no difference.

EXAMPLE 6

Measurement of Nicotine Decomposability by a Clinical Test

In order to verify the nicotine decomposability of the functional agent, a clinical test was carried out. In the clinical test, healthy twenty men (17 to 20 people) who smoke 15 to 25 tobaccos per day were test subjects and the tobacco was "THIS"(trademark, available in the market).

Figure 9:
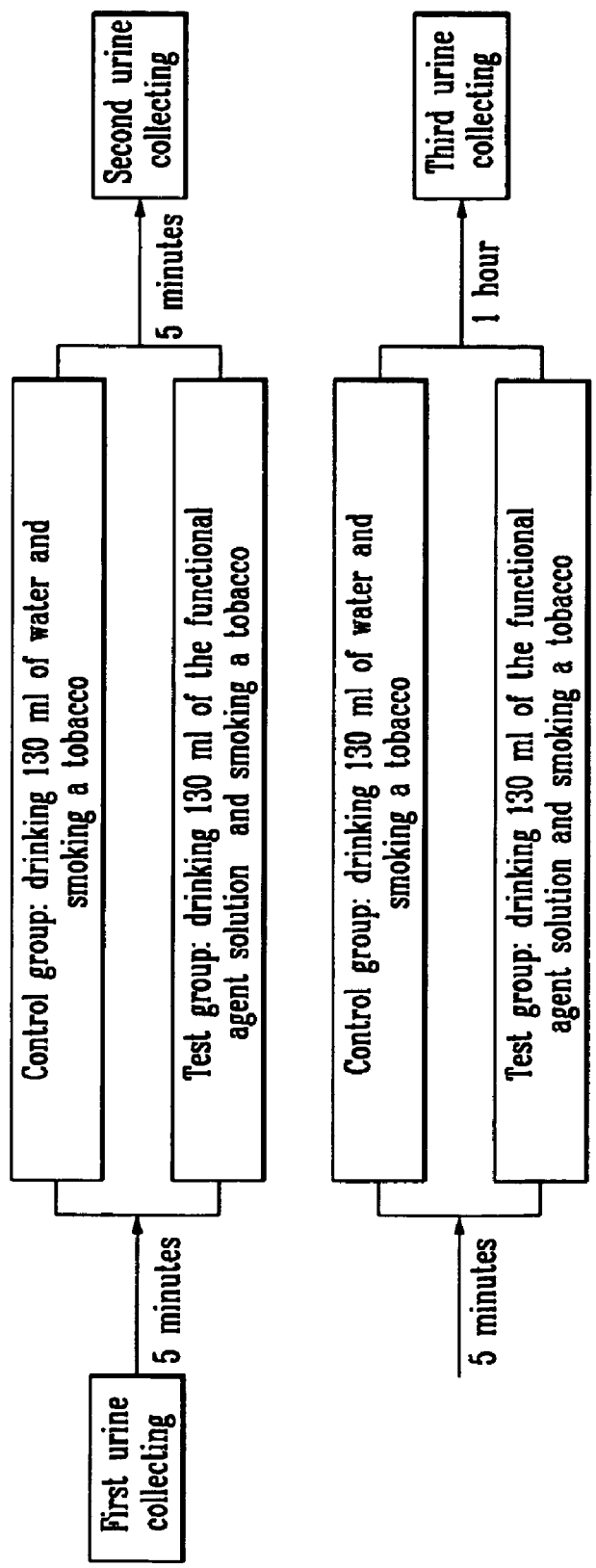
FIG. 9 is a diagram showing the clinical test method to test the nicotine decomposability of the functional agent of the present invention.

In order to ensure the test, the test was repeated several times and averaged. The test group drinking the functional agent and control group drinking water was tested on different days. If possible, the condition of a body and test time were consistent during the test. The test subjects smoked as usual and FIG. 9 shows the test method.

The collected first, second, and third urine was stored at −20° C. immediately. After 48 hours, cotinine that is an important metabolite of nicotine in urine was quantified. The detail method is as follows.

500 µl of urine or standard sample was placed in 1.5 ml tube. In order to ensure reliability of the test result, two tubes were used per sample. 250 µl of 4M sodium acetate buffer solution (pH 4.7), 100 µl of 1.5M KCN, 100 µl of 0.4M chloramine-T, 500 µl of 78 mM barbituric acid dissolved in 50% by volume of acetonitrile were added in turn into the sample and mixed for 10 seconds. The mixture was reacted at 100 rpm for 15 minutes at room temperature(25° C.) and the reaction was stopped after adding 100 µl of 1M sodium metabisulphite. Absorbance was measured at 490 nm and the sample was quantified in comparison with standard curve.

Figure 10A:
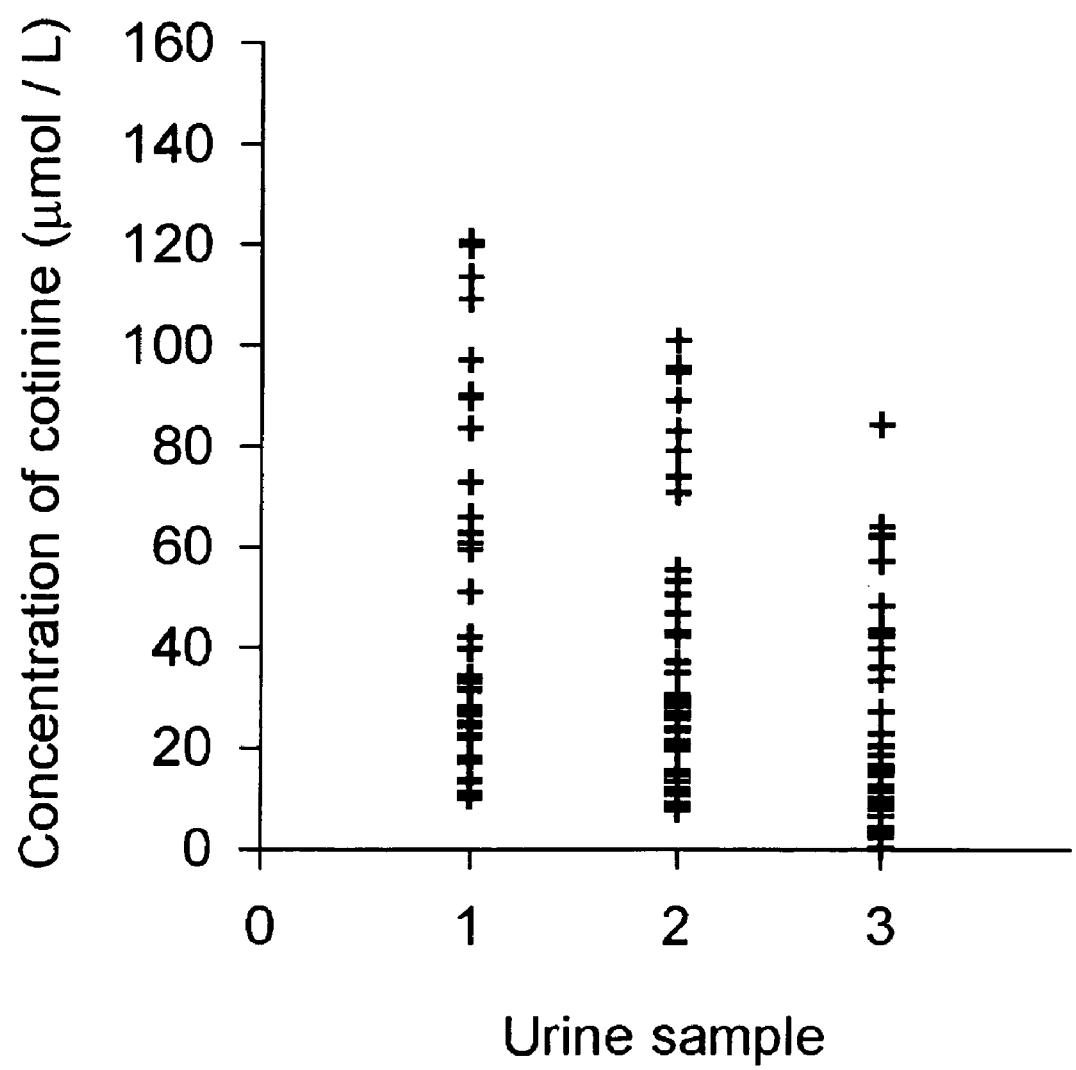
FIG. 10 is a graph showing cotinine concentration within urine of smokers ingested with the functional agent of the present invention (B) and smokers ingested with water as a control (A).
Figure 10B:
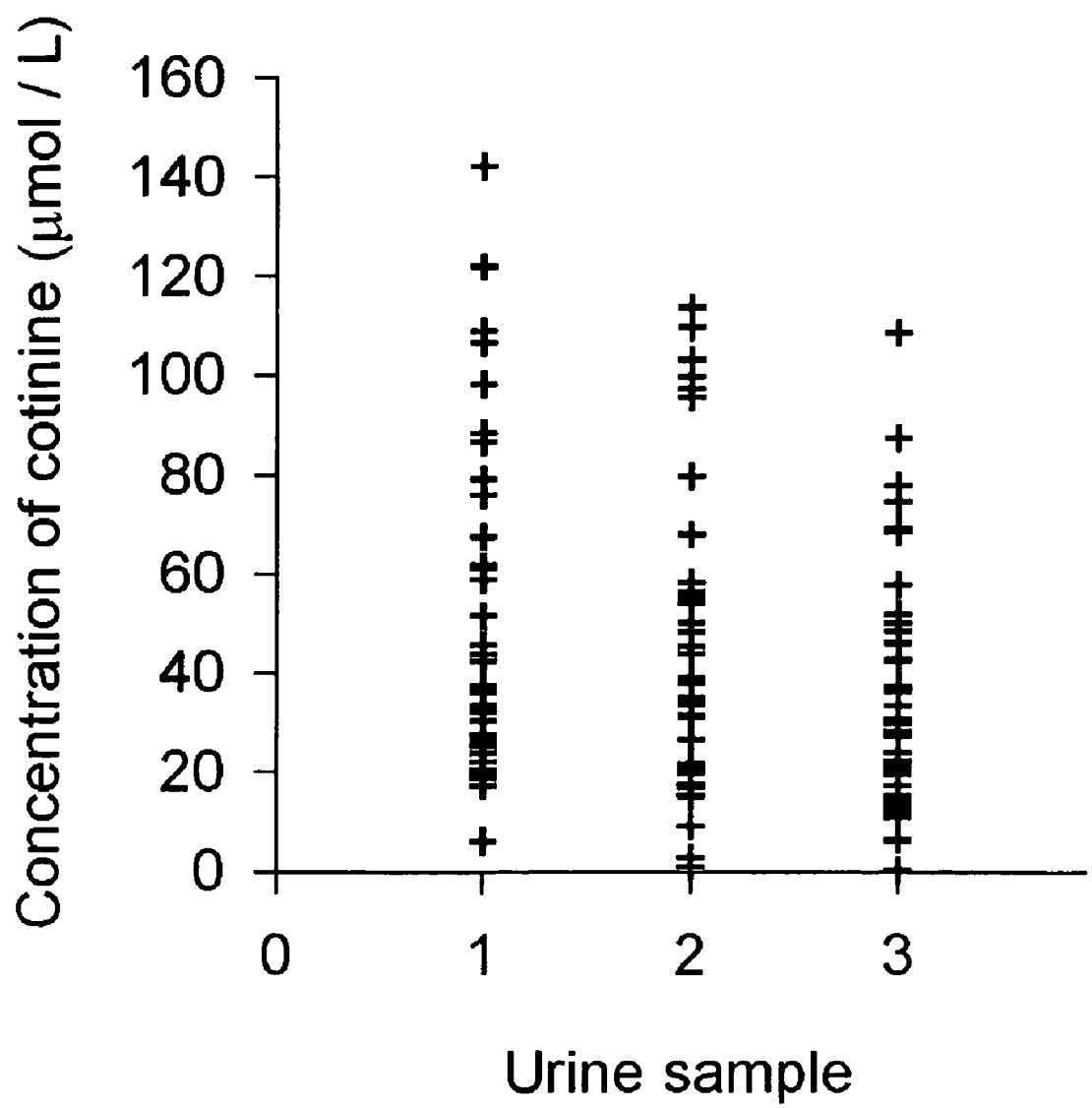

FIG. 10 is a graph showing the nicotine decomposability of smokers having ingested the functional agent for decomposing nicotine. (A) is a control, and after the test subjects drank water and smoked, cotinine in urine was quantified. (B) is quantified cotinine contained in urine after the test subjects drank the functional agent and smoked. The first, second and third urine were collected from 37 smokers.

Figure 11:
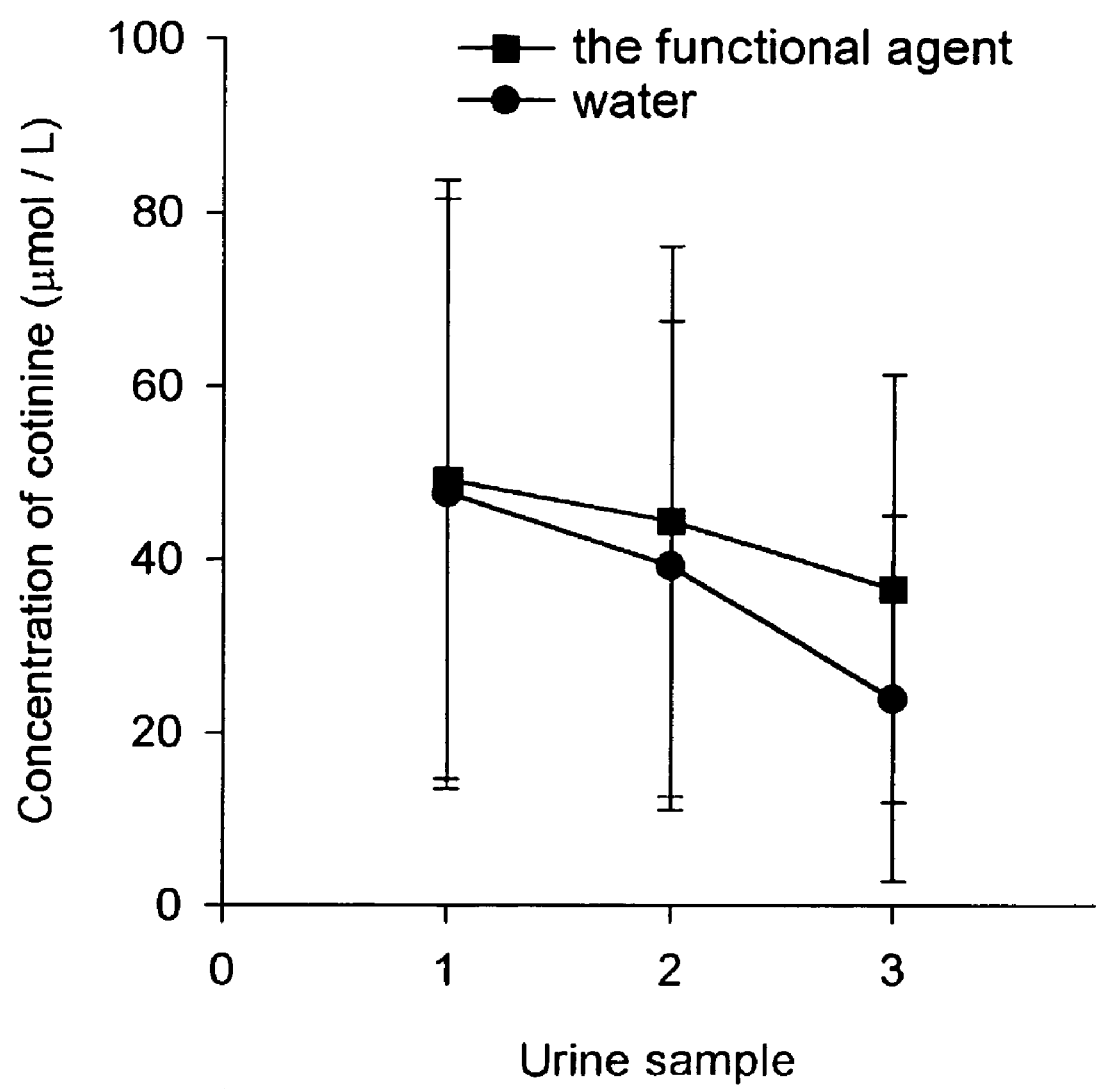
FIG. 11 is a graph showing the average cotinine concentration in urine of smokers ingested with the functional agent of the present invention and smokers ingested with water as a control.

FIG. 11 is a graph showing the average cotinine concentration of smokers having ingested the functional agent of the present invention. Since the group having ingested the functional agent has a greater amount of cotinine in urine than the control group, it is confirmed that nicotine decomposability by the functional agent is high.

Figure 12:
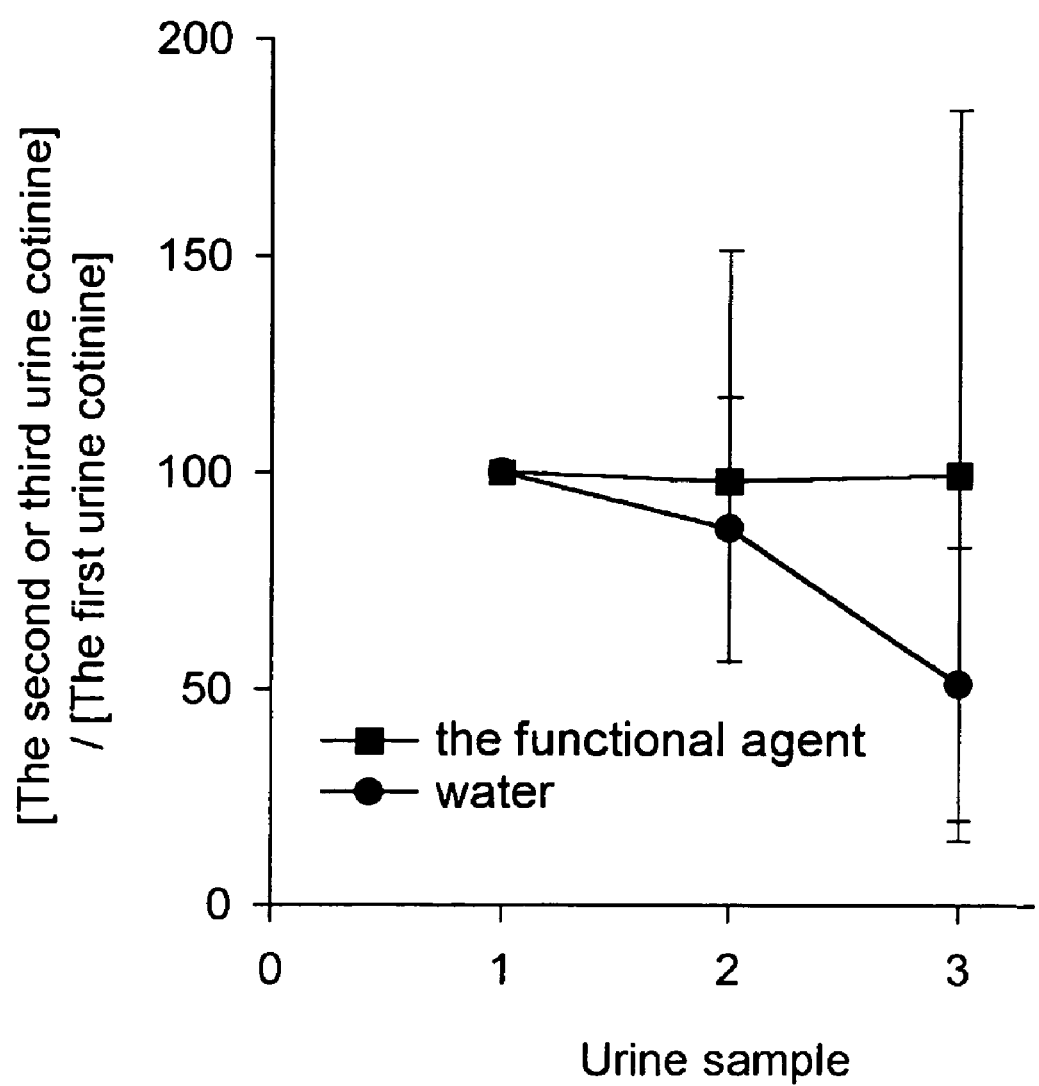
FIG. 12 is a graph which is an average value of cotinine contained in urine of smokers after drinking the functional agent or water per person.

FIG. 12 is a graph showing an average value of cotinine contained in urine of smokers who smoked after drinking the functional agent or water per person. The value of second or third urine divided by the first urine per person was averaged and compared the functional agent with water.

Nicotine decomposition rate was based on the cotinine generation of the second and third urine. When taking out the first, second and third urine, all cotinine remaining in urine was excreted so that it is confirmed that nicotine was decomposed into cotinine. Also, the nicotine decomposition rate (cotinine generation rate) of the test group is about two times that of the control group. This shows that the functional agent of the present invention facilitates the decomposition of nicotine to cotinine in a body.

In additionally tablet comprising the functional agent are prepared.

The healthy forty men (20 to 30 people) who have smoke over two years divide to two groups and tested for 2 days.

The test subjects smoked every hour for 8 hour and urine was collected five times. The test subjects of Group I were administrated three times with two tablets at a time, Group II were administrated once with six tablets, and urine was collected.

Test <Method>

Control (Group I and group II): water-drinking & smoking->after 1 hour 1st urine collection, water-drinking & smoking->after 1 hour 2nd urine collection, water-drinking & smoking->after 1 hour 3rd urine collection, water-drinking & smoking->after 1 hour, smoking->after 1 hour 4th urine collection, water-drinking & smoking->after 1 hour, smoking->after 1 hour, smoking->after 1 hour 5th urine collection.

Group I: taking two tablets, water-drinking & smoking->after 1 hour 1st urine collection, water-drinking & smoking->after 1 hour 2nd urine collection & smoking->after 1 hour 3rd urine collection, taking two tablets, water-drinking & smoking->after 1 hour, smoking->after 1 hour 4th urine collection, taking two tablets, water-drinking & smoking->after 1 hour, smoking->after 1 hour, smoking->after 1 hour 5th urine collection.

Group II: taking six tablets, water-drinking & smoking->after 1 hour 1st urine collection, water-drinking & smoking->after 1 hour 2nd urine collection & smoking->after 1 hour 3rd urine collection, water-drinking & smoking->after 1 hour, smoking->after 1 hour 4th urine collection, water-drinking & smoking->after 1 hour, smoking->after 1 hour, smoking->after 1 hour 5th urine collection.

The collected urine was stored at −20° C. immediately. After 48 hours, cotinine that is an important metabolite of nicotine in urine was quantified.

TABLE 1

| | 1st | 2nd | 3rd | 4th | 5th |
|---|---|---|---|---|---|
| Control Average value of cotinine in Group I(μM) | 16.46 | 10.84 | 12.59 | 13.84 | 9.98 |
| Average value of cotinine in Group II(μM) | 34.86 | 15.48 | 21.49 | 28.59 | 19.14 |
| Average value of cotinine in Group I(μM) | 19.29 | 11.95 | 18.51 | 18.88 | 16.32 |
| Average value of cotinine in Group II(μM) | 42.26 | 31.37 | 32.72 | 36.72 | 25.48 |
| Increase of cotinine in Group I(%) | 17.2 | 10.2 | 47.0 | 36.4 | 63.5 |
| Increase of cotinine in Group II(%) | 21.2 | 102.6 | 52.3 | 28.4 | 33.1 |

When the tablet was administrated, cotinine value in urine increased by 60 to 100% compared to drink only water. The collected urine from Group I contained cotinine at a fixed concentration during test period and cotinine concentration in the urine from Group II was almost identical to that of the control group after 10 hr.

EXAMPLE 7

Inhibition Effect for Nitrosomorpholine Generation by the Functional Agent

The present test relates to an in vitro test concerning whether the functional agent inhibits the generation of the above carcinogen when nitrosating agents such as nitrous acid, nitrite ester, thioester, anhydrous nitrous acid, nitrosyl halide, nitrosyl metal, and inorganic metal nitrite complexes, react with amine or a compound containing other nitrogen to form carcinogen such as nitrosamine or N-nitroso compound.

The test was based on U.S. Pat. No. 5,087,671 (polymers for scavenging nitrosating agents) and carried out by applying DBA(direct barbituric acid) method which detects cotinine from urine, and pre-treatment method of gas chromatography (Joseph, D., Lajos H., Nigel, H., Stanley, I. R., and Timothy, T. (1992) J. Chromatogr., 579, 93–98).

Nitrosamine byproducts are mainly a reaction result of amine and nitrosating agent. First nitrosating agent is formed from nitrite such as sodium nitrate ($NaNO_2$) or potassium nitrate ($KNO_2$) in acid and the formed product is nitric acid($HNO_2$).

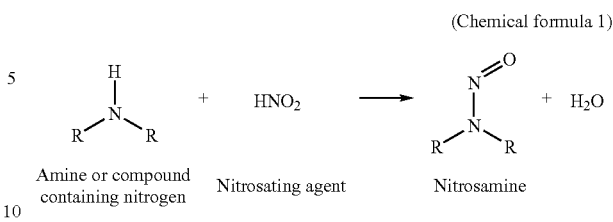

(Chemical formula 1)

Amine or compound containing nitrogen    Nitrosating agent    Nitrosamine

EGCG, quercetin, catechin, vitamin C and powdered green tea were used as a control group. Each specimen was used in a concentration of 2.5, 5, 10, 15, 20 mg/ml. 200 mM of sodium nitrate not containing morpholine was used as a negative control. The specimen not containing the nitrosating agent $NaNO2$ was used as a blank in each reaction.

Figure 13:
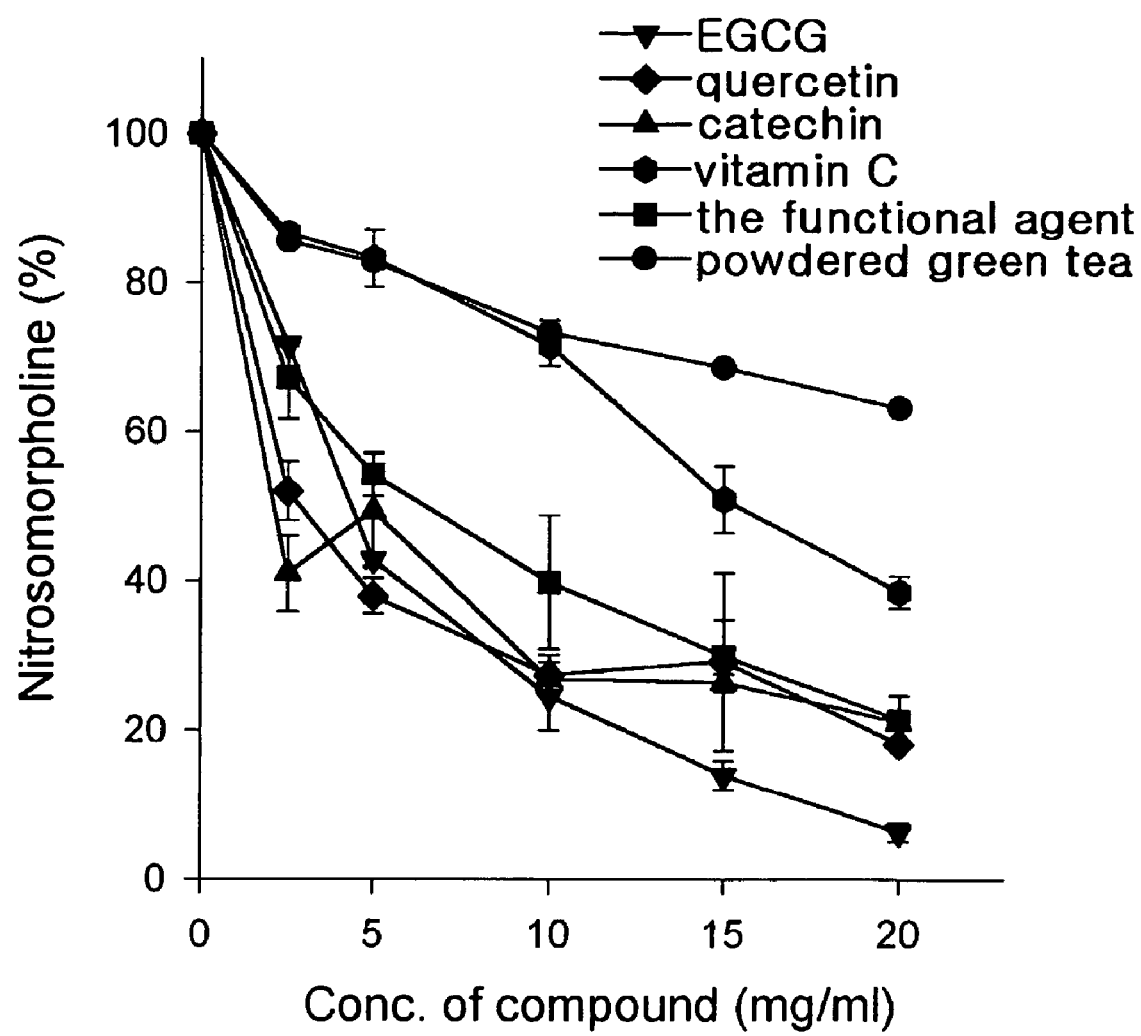
FIG. 13 is a graph showing the inhibition effect for the generation of nitrosomorpholine by the functional agent, powdered green tea, EGCG (epigallocatechin-3-gallate), quercetin, vitamin C, and catechin.

Each specimen was added into 15 ml of corning tubes according to concentration and marked with the blank, test, negative control. 1 ml of glacial acetic acid was added into each tube and 100 μl of 2 M $NaNO_2$ was added into each tube except blank and distilled water was added to make total volume of 2 ml. After reacting for 10 minutes at 37° C., 176 μl of morpholine was added to make 2 M and the reaction was further carried out for 30 minutes at 37° C. The reaction was stopped by adding 3.8 ml of 5 N NaOH to set pH 10 to 12. According to DBA method, the specimens were measured and compared with blank group (not added $NaNO_2$) and negative control group (not added morpholine and added 200 mM $NaNO_2$). The result is shown in FIG. 13.

Generation rate of nitrosomorpholine (NMOR %) is measured as below calculating formula 1.

NMOR %=[($t_0$−blank)−($t_{30}$−blank)]/ ($t_0$−blank)    (Calculating formula 1)

Blank; a specimen not containing nitrosating agent $NaNO_2$ $t_0$; a specimen containing 200 mM of $NaNO_2$ without morpholine $t_{30}$; a specimen normally reacted in the generation of nitrosomorpholine.

As shown in FIG. 13, the functional agent for decomposing nicotine of the present invention showed 75% inhibition of generating nitromorpholine from morpholine at 20 mg/ml concentration like purified quercetin or catechin. That is, the functional agent of the present invention inhibits generation of carcinogenic nitroso-compound.

EXAMPLE 8

Figure 14:
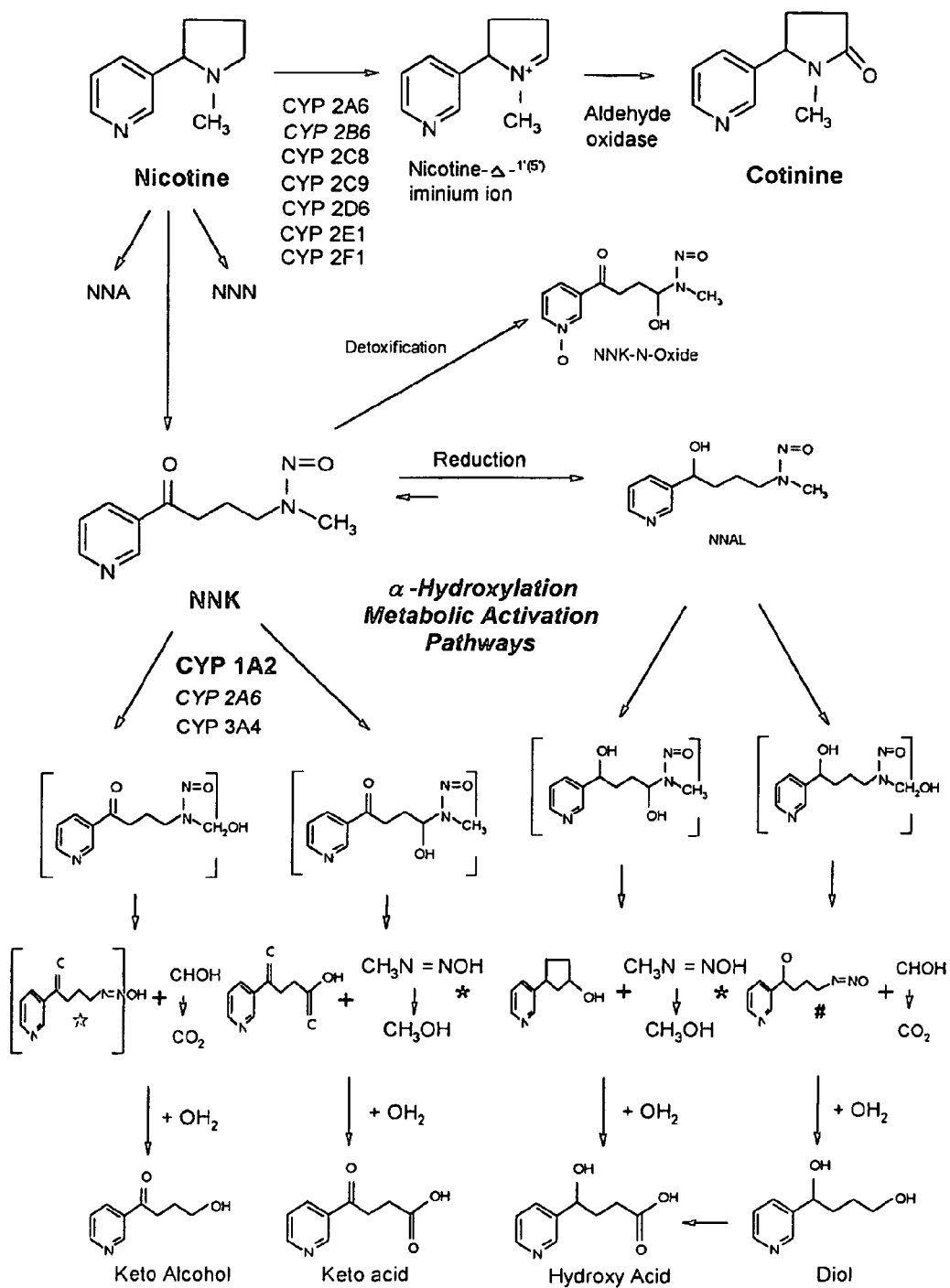
FIG. 14 is a diagram showing the metabolism of nicotine.
Figure 15A:
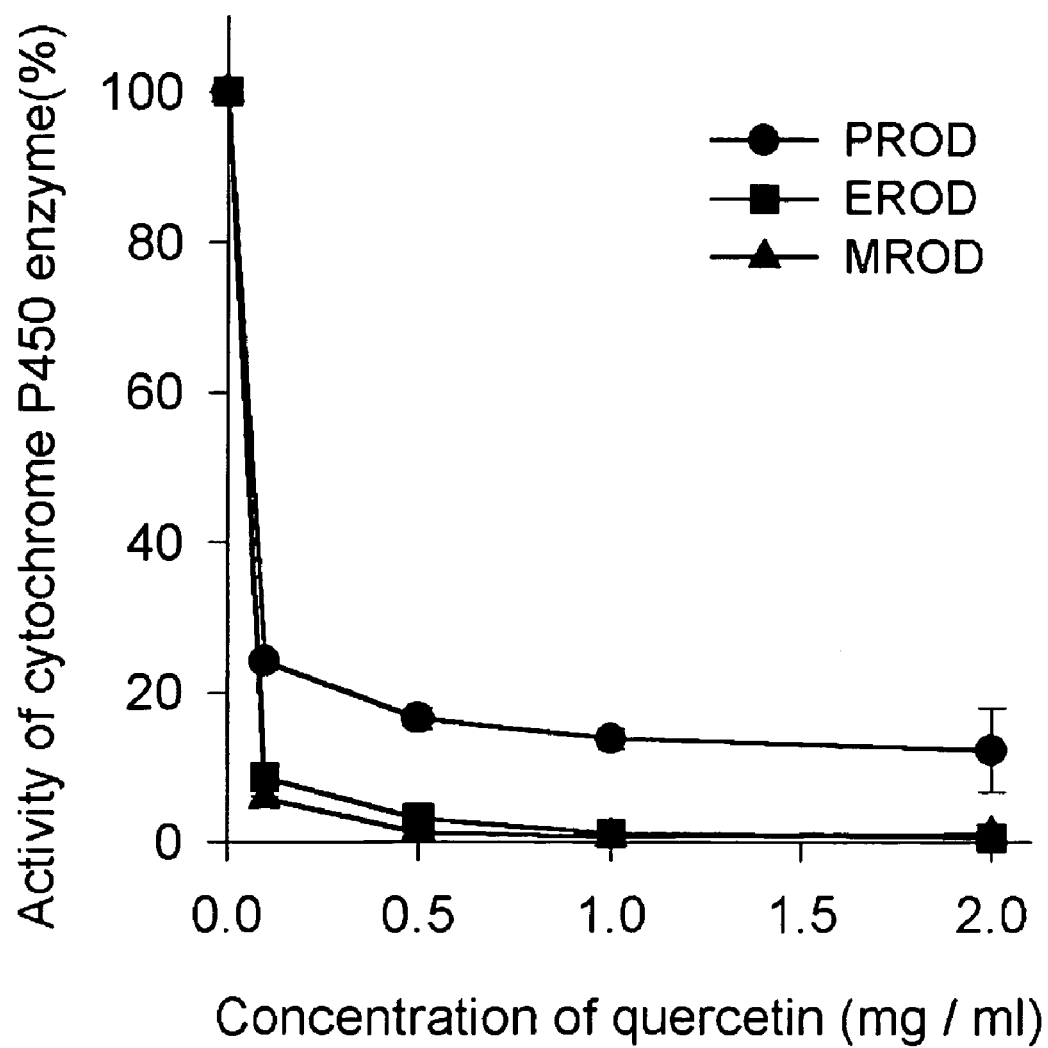
FIG. 15 is a graph showing the inhibition effect for CYP enzyme activity by the functional agent, quercetin, catechin and powdered green tea.
Figure 15B:
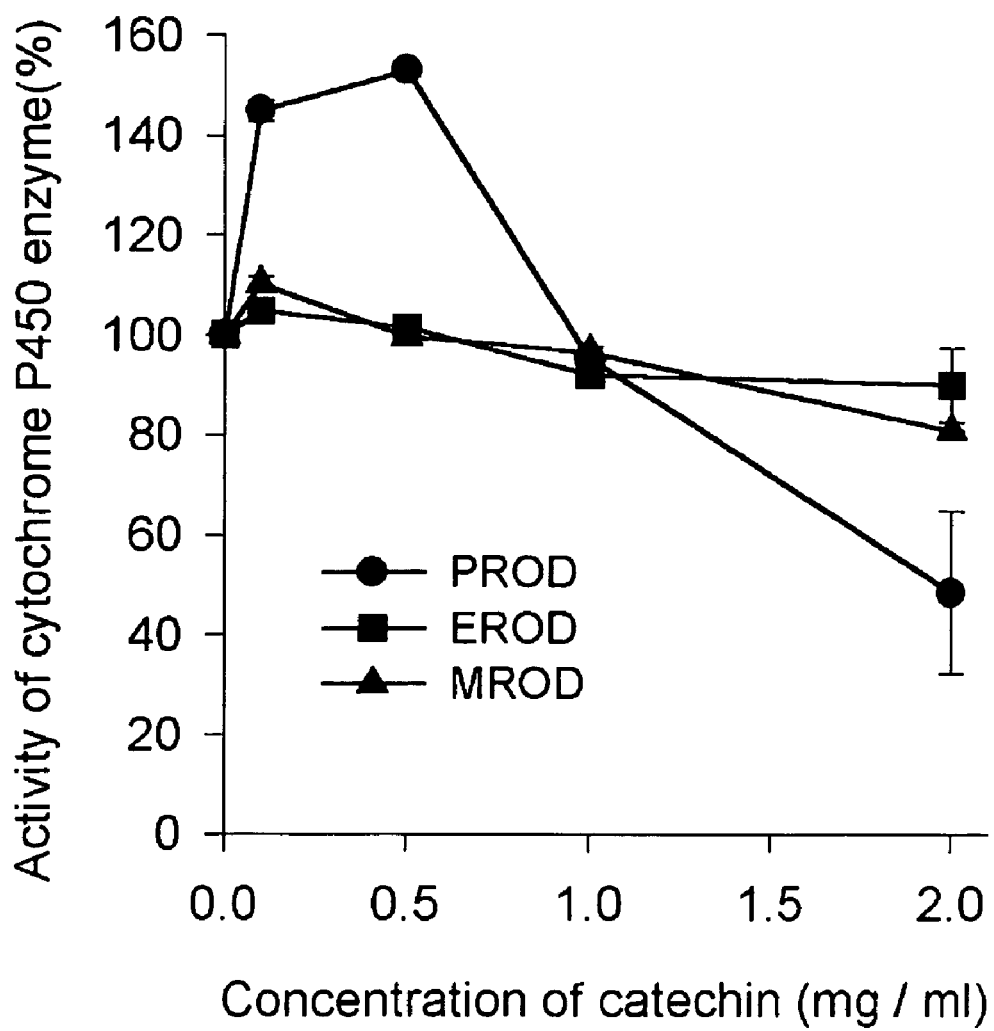
Figure 15C:
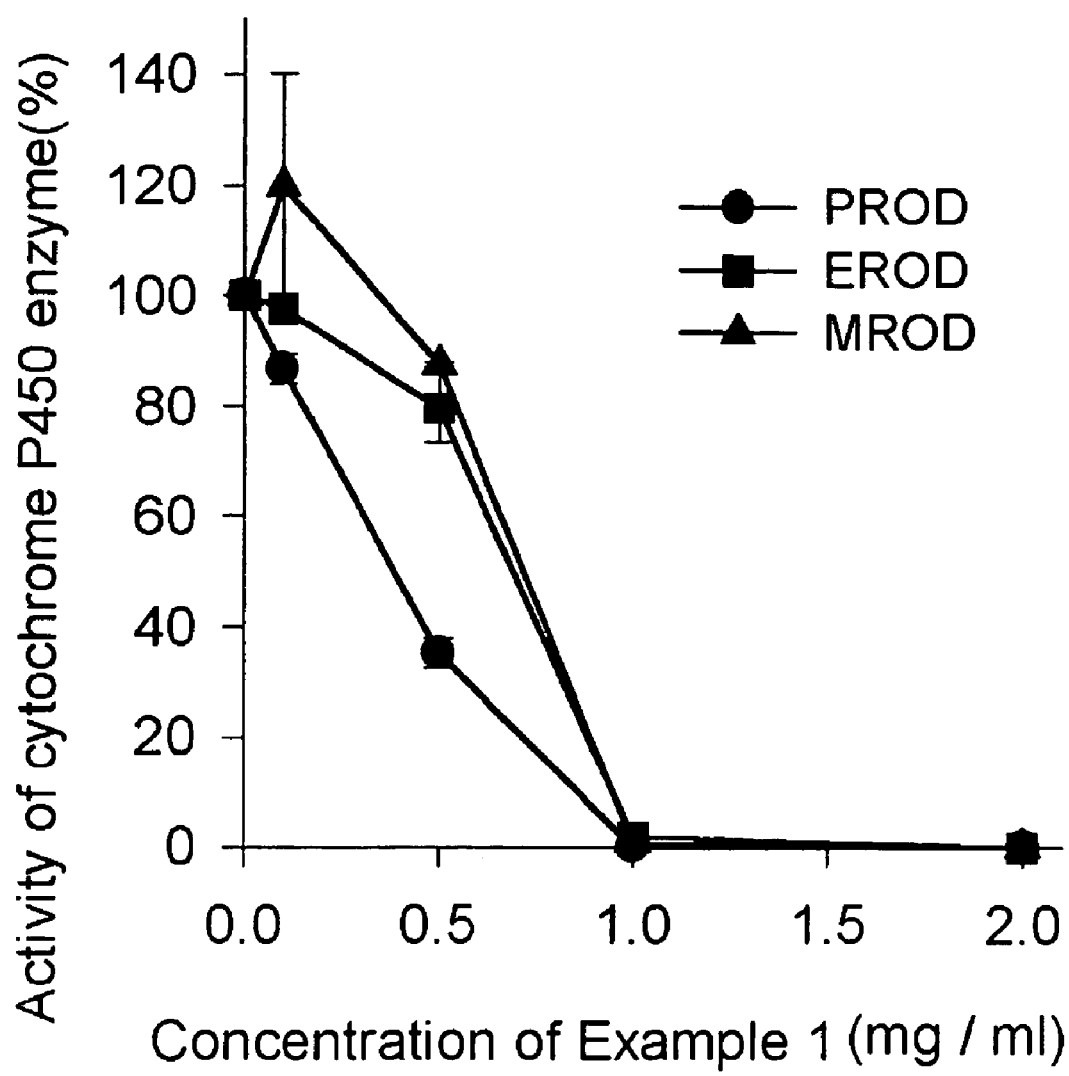
Figure 15D:
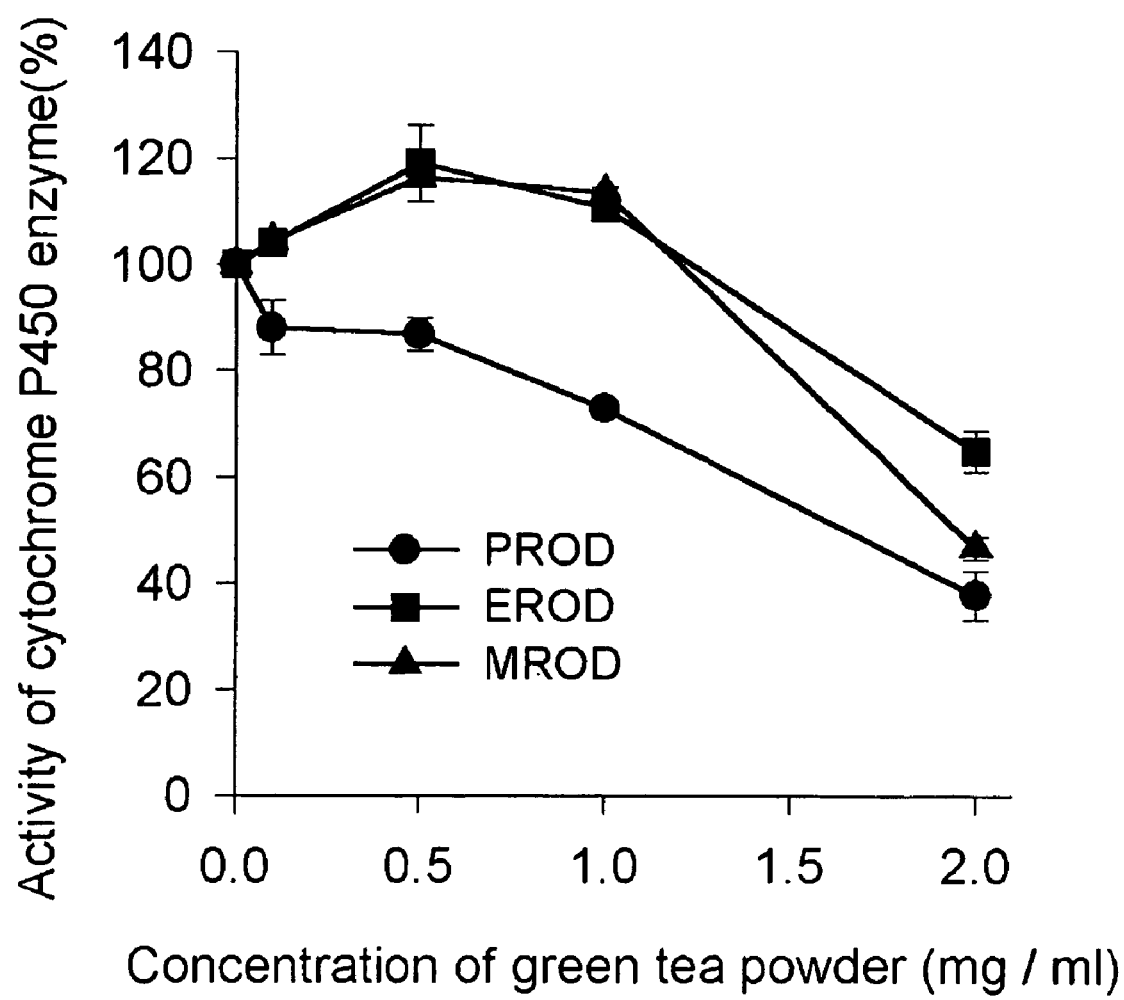

Test of Inhibition Effect for Cytochrome $P_{450}$ Activity by the Functional Agent for Decomposing Nicotine Cytochrome $P_{450}$ (hereinafter, "CYP") is a main enzyme employing detoxication in a lung or liver. Various kinds of CYP have each different function in a liver and of these CYP 2A6, 2B6, 2C8, 2C9, 2D6, 2E1, 2F1 are related to metabolism of cotinine from nicotine (Yamazaki, H., Inui, Y., Yun, C. H., Guengerich, F. P., and Shimada, T. (1992) Carcinogenesis, 13, 1789–1794; Code, E., Crespi, C., Penman, B., Gonzalez, F., Chang, T., and Waxman, D. (1997) Drug Metab. Dispos., 25, 985–993). NNK is a pro-carcinogen in laboratory animals and it is metabolized to carcinogen by CYP 1A2, 2A6, and 3A4. FIG. 14 shows metabolism of nicotine.

The present test measured the inhibition effect of CYP relating to NNK activation to various test materials after inducing CYP of a liver from a rat(Sprague-Dawley rat) by Aroclor 1254(Sigma, USA) and taking out the liver. The detailed test method is as followed.

Aroclor 1254 was injected into the abdomen of a 7-week old male rat (Sprague-Dawley rat) in a capacity of 500 mg/kg. After 5 days, the liver was taken out in a sterile state and homogenized using 0.15M of KCl solution at 4° C. A supernatant was separated by a centrifugal separation for 10 minutes at 9000 g from the homogenate and used in the test. Activity of CYP was measured by using pentoxyresorufin (Sigma USA) which is a substrate of CYP 2B1/2/4, ethoxyresorufin(Sigma USA) which is a substrate of CYP 1A1 and methoxyresorufin(Sigma USA) which is a substrate of CYP 1A2. Also, EGCG, quercetin, catechin and powdered green tea were used as a control group and compared with the functional agent of Example 1. The inhibition effect for CYP activity was compared using the above reaction specimen (inhibition material), the supernatant taken out from the liver and specific substrate of each CYP. If the substrate is decomposed by an enzyme and shows fluorescence, enzyme activity is measured by a spectrofluoro photomete (excitation at 522 nm and emission at 586 nm). Each specimen has a concentration of 0.1, 0.5, 1.0 and 2.0 mg/ml and an amount of protein taken out from the liver is set to 500 µg/ml. Each substrate had 2.5 µM of stock solution and finally became 25 nM after adding 10 µl. 20 µl of 5 mM β-NADPH(Sigma, USA) was used as coenzyme. And then, the final volume was made to 1 ml by using 50 mM Tris-HCl(pH 7.4) buffer solution. The reaction was carried out at 37° C. for 20 minutes, stopped after adding 2 ml of methanol and centrifugal separated at 2000 rpm for 2 minutes. The enzyme activity was measured by using a RF-5301 PC spectrofluoro photometer (SHIMADZU, Japan) from the supernatant (excitation at 522 nm and emission at 586 nm). FIG. 15 shows the result.

FIG. 15 is a graph showing whether the functional agent for decomposing nicotine of the present invention affects CYP enzyme activity. (A) shows CYP inhibition effect of quercetin, (B) shows for catechin, (C) shows for the functional agent, and (D) shows for powdered green tea. PROD means pentoxyresorufin dealkylase (CYP 2B1/2/4), EROD means ethoxyresorufin dealkylase(CYP 1A1), and MROD means methoxyresorufin dealkylase(CYP 1A2). The functional agent inhibited all of PROD, EROD and MROD.

Figure 16:
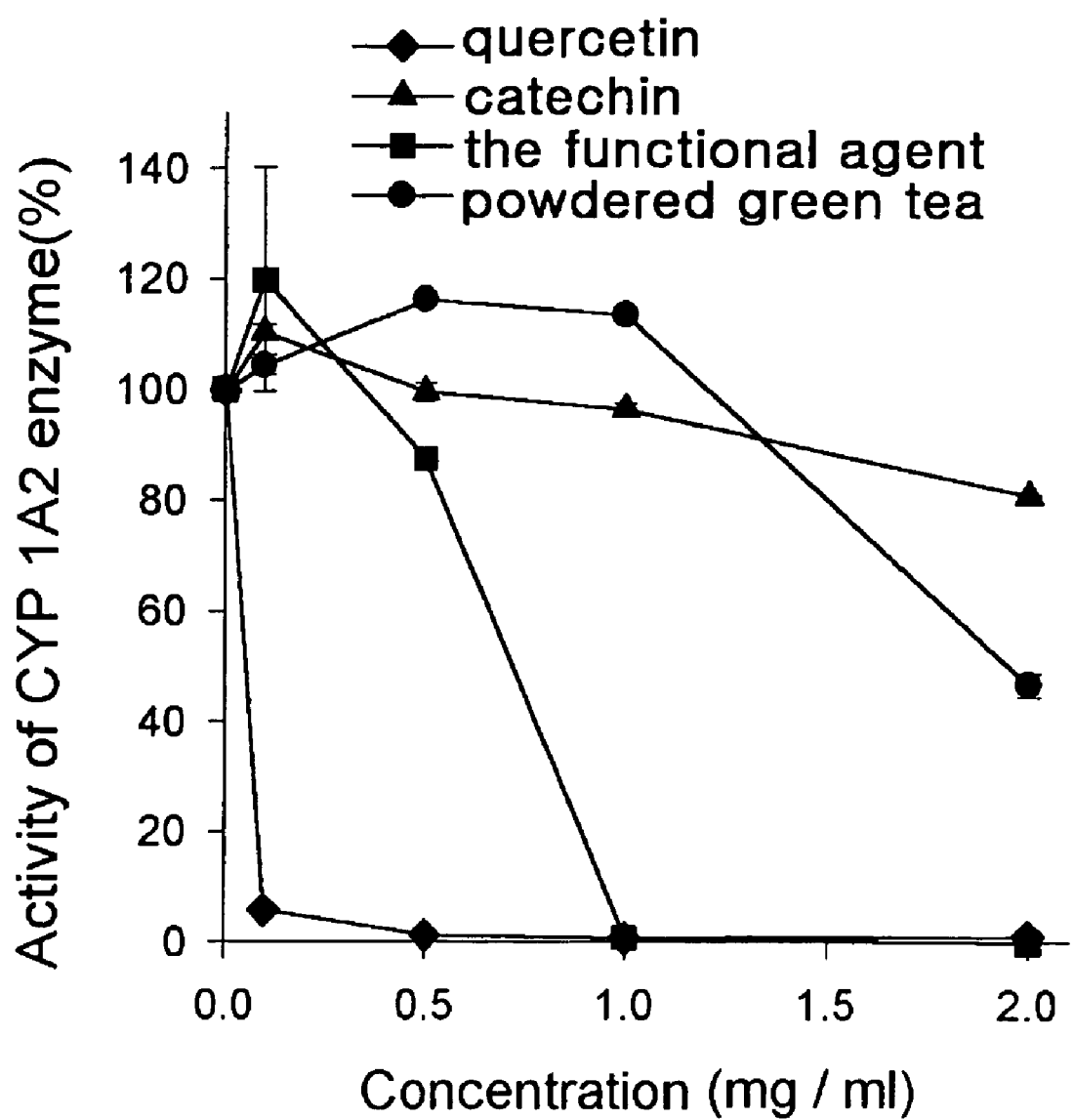
FIG. 16 is a graph showing the inhibition effect for CYP 1A2 enzyme activity by the functional agent, quercetin, catechin and powdered green tea.

FIG. 16 shows the inhibition effect for activity of CYP 1A2 enzyme by the functional agent of the present invention. The activity of CYP 1A2 was inhibited in order of quercetin>>the functional agent>>catechin≈powdered green tea. It was confirmed that 1.0 mg/ml of the functional agent completely inhibited activity of CYP 1A2.

In addition, the inhibition effect for enzyme activity by the functional agent, EGCG, quercetin, catechin and powdered green tea was measured by using purified RECO® System CYP 1A2(PanVera Co, USA).

A composition of enzyme mixture comprises 0.5 uM CYP1A2, 0.2 µM NADPH $P_{450}$ reductase, 0.5 µg/uL CHAPS, 0.1 µg/uL liposomes (dilauroyl phosphotidylcholine, dileoyl phosphotidylcholine, dilauroyl phosphotidylcholine (1:1:1)), 3 mM reductive glutathion, and 50 mM HEPES/KOH (pH 7.4). A buffer solution is 1 M potassium/sodium phosphate. 768 µl of tertiary distilled water, 126.7 µl of CYP 1A2 buffer solution, and 5.3 µl of 1 mM methoxyresorufin were added sequentially to make 950 µl of solution and heated at 37° C. 5 µl of enzyme activation inhibiting material was added into 85 µl of buffer solution and substrate mixture to make final concentration 0.1, 0.5, 1.0, and 2.0 mg/ml respectively. The reaction started at 37° C. while adding 5 µl of CYP 1A2 enzyme mixture and 5 µl of 50 mM NADPH. The reaction was maintained for 20 minutes and stopped by adding 1 ml of methanol. The enzyme activity was measured by using a RF-5301 PC spectrofluoro photometer (SHIMADZU, Japan).

Figure 17A:
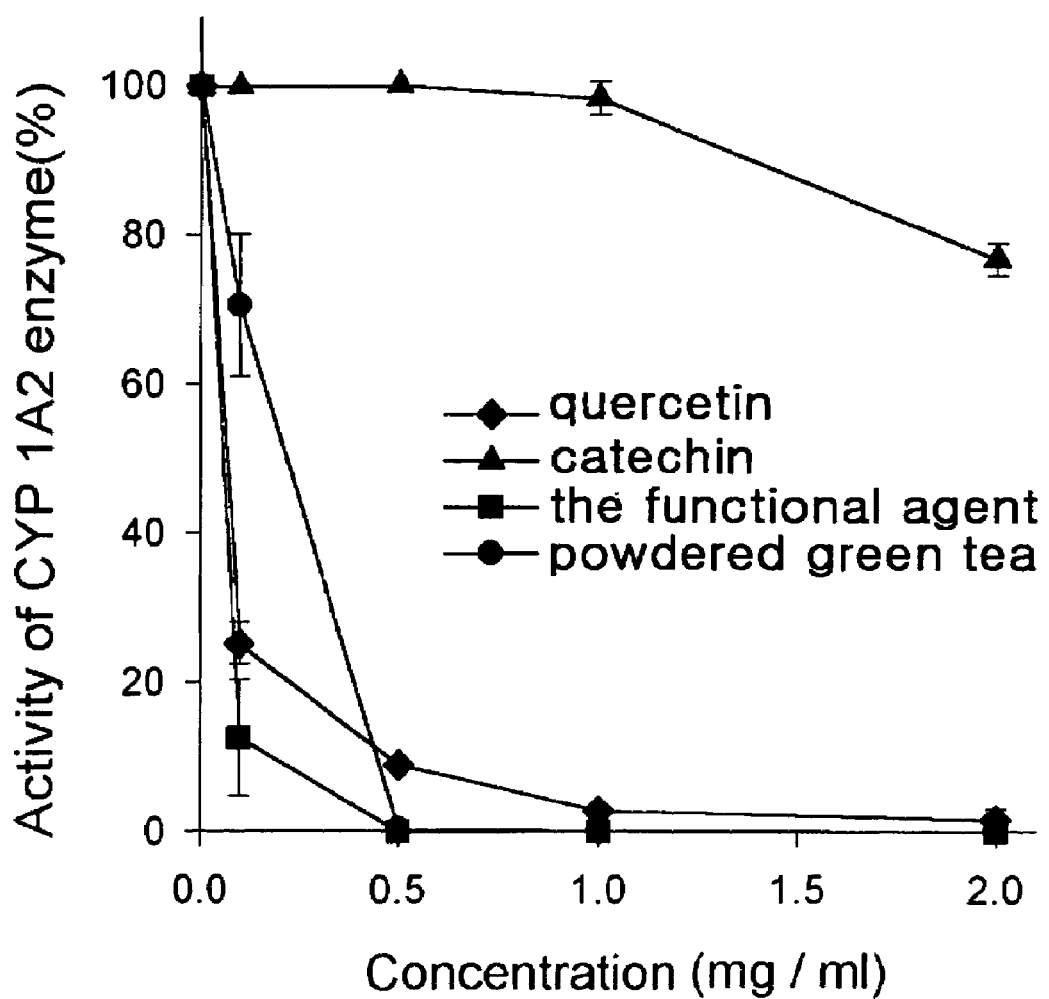
FIG. 17 is a graph showing the inhibition effect for purified CYP 1A2 enzyme activity by the functional agent, EGCG, quercetin, catechin and powdered green tea at high concentration (A) and low concentration (B).
Figure 17B:
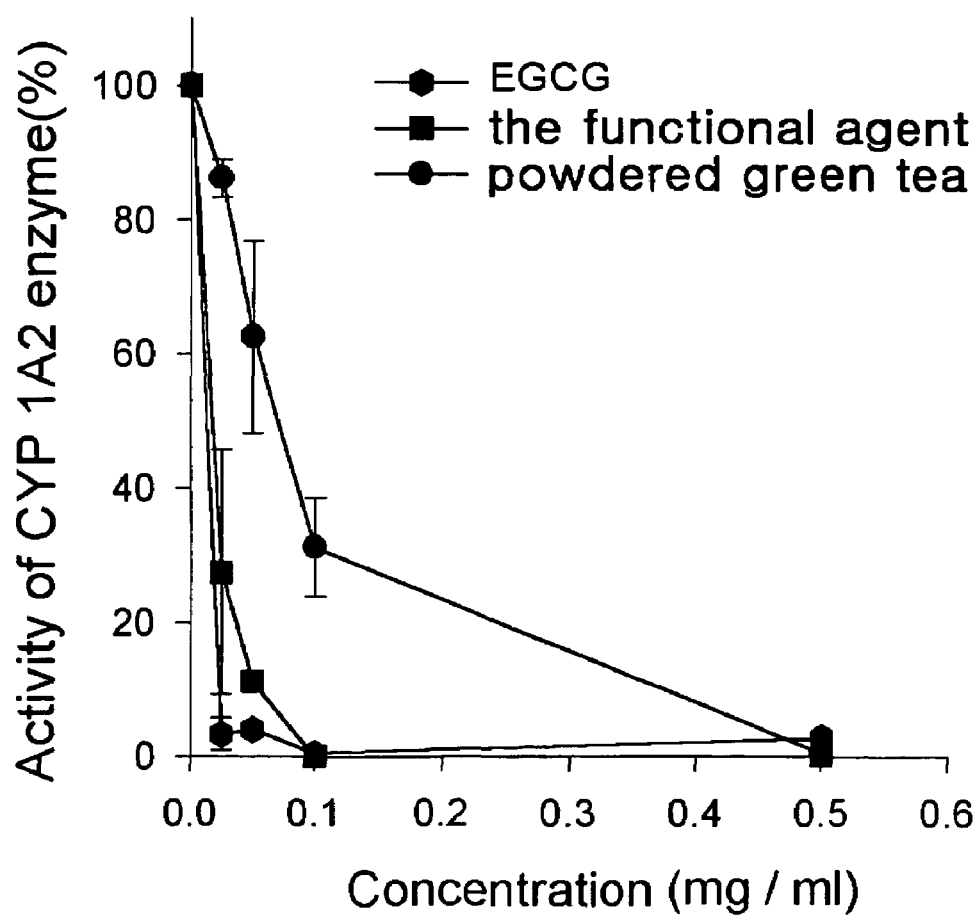
Figure 18A:
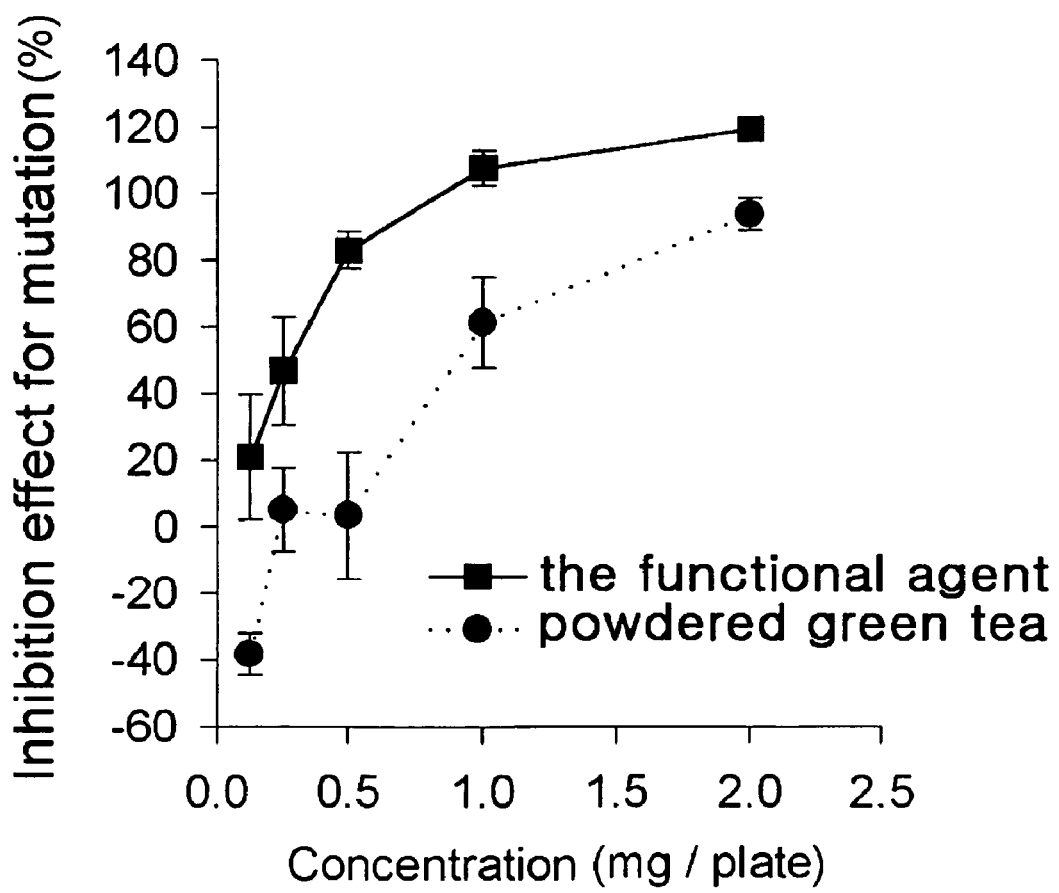
FIG. 18 is a graph showing the inhibition effect for mutagenicity of NNK by the functional agent, quercetin, catechin and powdered green tea.
Figure 18B:
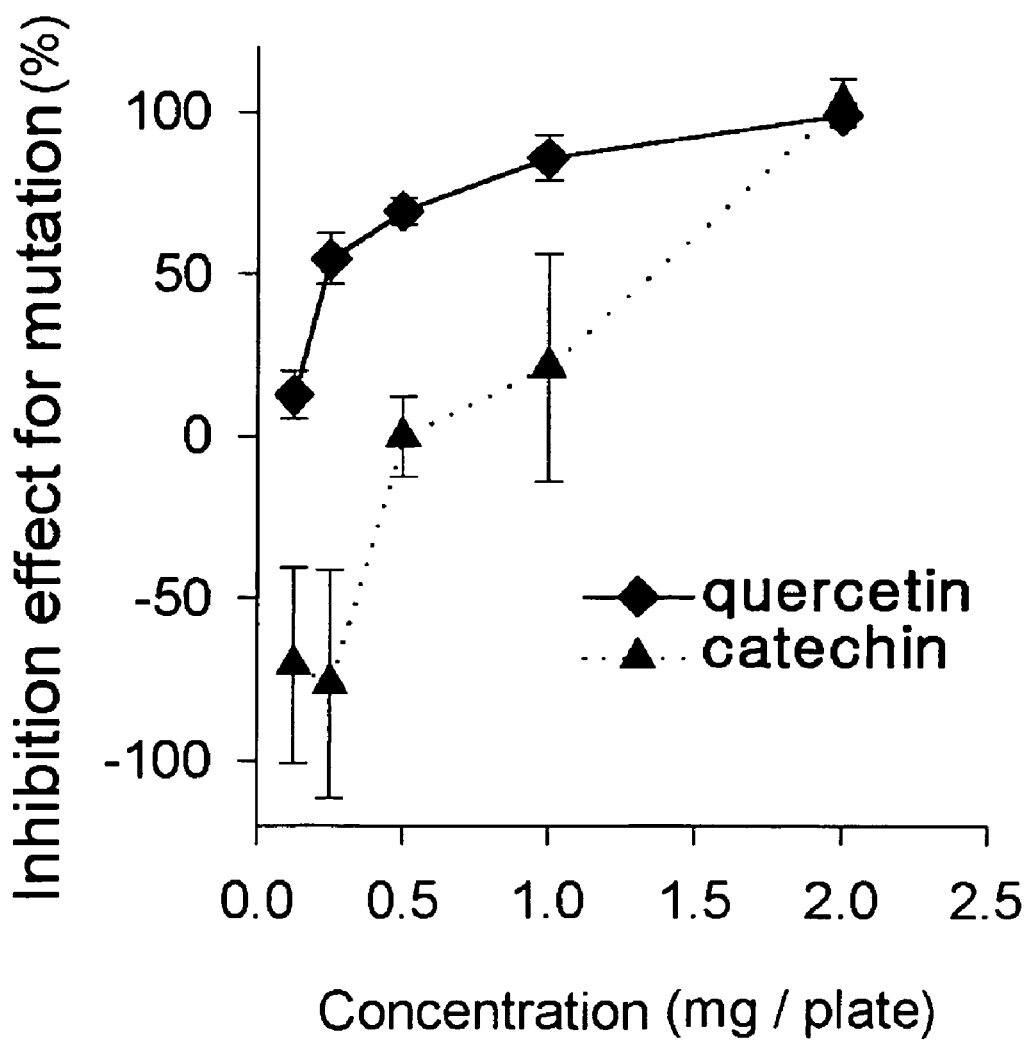
Figure 18C:
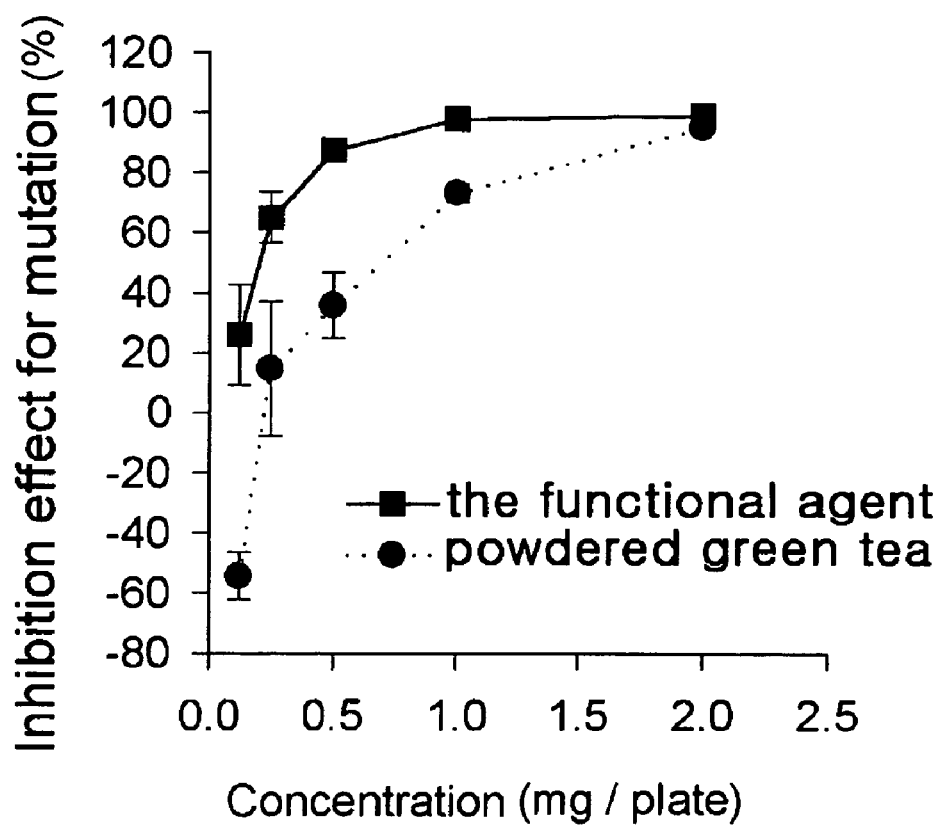
Figure 18D:
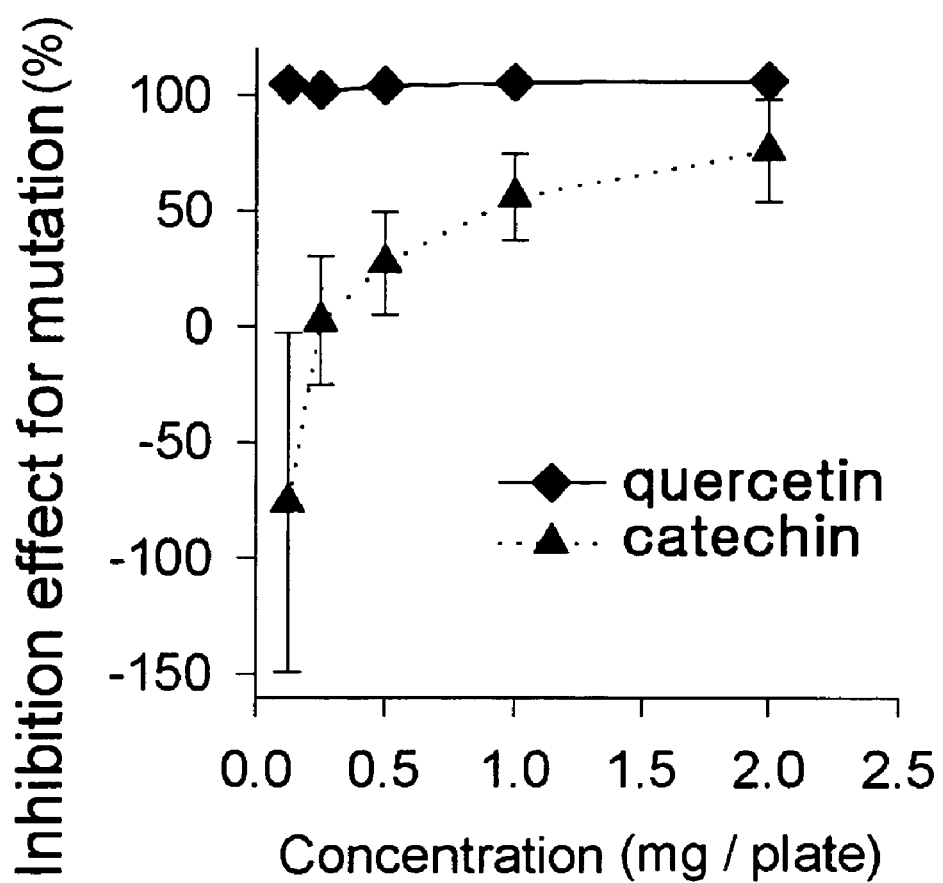

FIG. 17 is a graph showing the inhibition effect for activity of purified CYP 1A2 enzyme by the functional agent of the present invention. The activity of CYP 1A2 was inhibited in order of EGCG>>the functional agent>>quercetin>>powdered green tea>>catechin. It was confirmed that 0.1 mg/ml of the functional agent (■) completely inhibited enzyme activity of pure CYP 1A2.

EXAMPLE 9

Effect of Anti-Mutation by the Functional Agent for Decomposing Nicotine

NNK (4-methylnitrosoamino-1-3-pyridyl-1-butanone) is contained in a tobacco in a determined concentration (about 0.1–0.5 ng) and also formed when nicotine is metabolized in a body. This is a very toxic material in a body. NNK is metabolized by an enzyme such as $P_{450}$ in a body to induce lung cancer. Also, benzopyrene is contained in tobacco in small amounts and acts as a mutagen.

In order to confirm whether the functional agent of the present invention has the effect of anti-mutation which inhibits mutation induced by NNK (Chemsyn. Lab. USA) and benzopyrene (Sigma, USA), Ames test was carried out by using *Salmonella typhimurium* TA100 and TA1535 which are histidine-requiring bacteria strain (Maron, D., Ames, B. N. (1983) Revised methods for the Salmonella mutagenicity test. *Mutation Research*, 113, 173– 215).

Aroclor 1254(Sigma, USA) was injected into an abdomen of 7-weeks old male rat (Sprague-Dawley rat) in a capacity of 500 mg/kg. After 5 days, a liver was taken out in a sterile state and homogenized using 0.15M of KCl solution at 4° C. A supernatant was separated by a centrifugal separation for 10 minutes at 9000 g from the homogenate to prepare S-9 mixture solution and used in the test. A composition of S-9 mixture solution is 5 ml of 0.2M phosphate buffer solution (pH 7.4), 0.4 ml of 0.1 M NADP, 0.05 ml of 1M glucose-6-phosphate, 0.2 ml of 0.4 m $MgCl_2$, 1.65M KCl, 3.35 ml of tertiary distilled water and 1 ml of liver based on 10 ml of S-9 mixture solution. The test materials were EGCG, quercetin, catechin, powdered green tea and the functional agent, and they were used after filtration by a 0.2 µm filter.

*Salmonella typhimurium* TA100 and TA1535 were cultured in a nutrient culture medium (Difco. Lab. USA) for 12 hours. 0.1 me of 12 hours-cultural solution, 0.1 ml of test material, 0.5 ml of S-9 mixture solution, 0.1 ml of NNK (10 mg/ml) or 0.1 ml of benzopyrene (20 µg/ml) were mixed. The effect test material was treated to have a concentration of 2, 1, 0.5, 0.25, 0.125 µg/plate. After standing the mixture solution at 37° C. for 20 minutes, 2 ml of supernatant agar(containing 0.05 mM histidine, 0.05 mM biotin) was added and they were spread to His⁻ plate medium. The plate medium has 3 sheets per capacity. After culturing at 37° C. for 48 hours, the number of colonies which were recovered mutants was recorded. Anti-mutation activity was indicated as the inhibition rate of His⁺ recovered mutants. The inhibition effect for mutation was converted according to the following calculating formula 2.

Inhibition effect for mutation (%)=
100×[(a−b)/(a−c)]        (Calculating formula 2)

a: number of colonies which are His⁺ recovered mutants induced by mutagen.

b: number of colonies which are His⁺ recovered mutants induced by mutagen and test material c: number of colonies which are spontaneously His⁺ recovered mutants FIG. 18 shows a result of inhibition effect for mutagenicity of NNK by the functional agent for decomposing nicotine of the present invention. (A) and (B) show inhibition effect for mutation of Salmonella typhimurium TA100 by the functional agent(■), powdered green tea(●), quercetin(♦), and catechin(▲). (C) and (D) show inhibition effect for mutation of *Salmonella typhimurium* TA1535 by the functional agent(■), powdered green tea(●), quercetin (♦), and catechin(▲). The concentration of NNK contained in the medium was 1 mg/plate.

The number of spontaneously recovered mutants of *Salmonella typhimurium* TA100 which were treated with only NNK was 173±13 and the number of spontaneously recovered mutants of *Salmonella typhimurium* TA1535 was 39±12. On the contrary, when NNK and 0.5 mg/plate of the functional agent were treated, the colonies of *Salmonella typhimurium* were hardly formed. Accordingly, it can be confirmed that there is an inhibition effect for mutation.

Figure 19A:
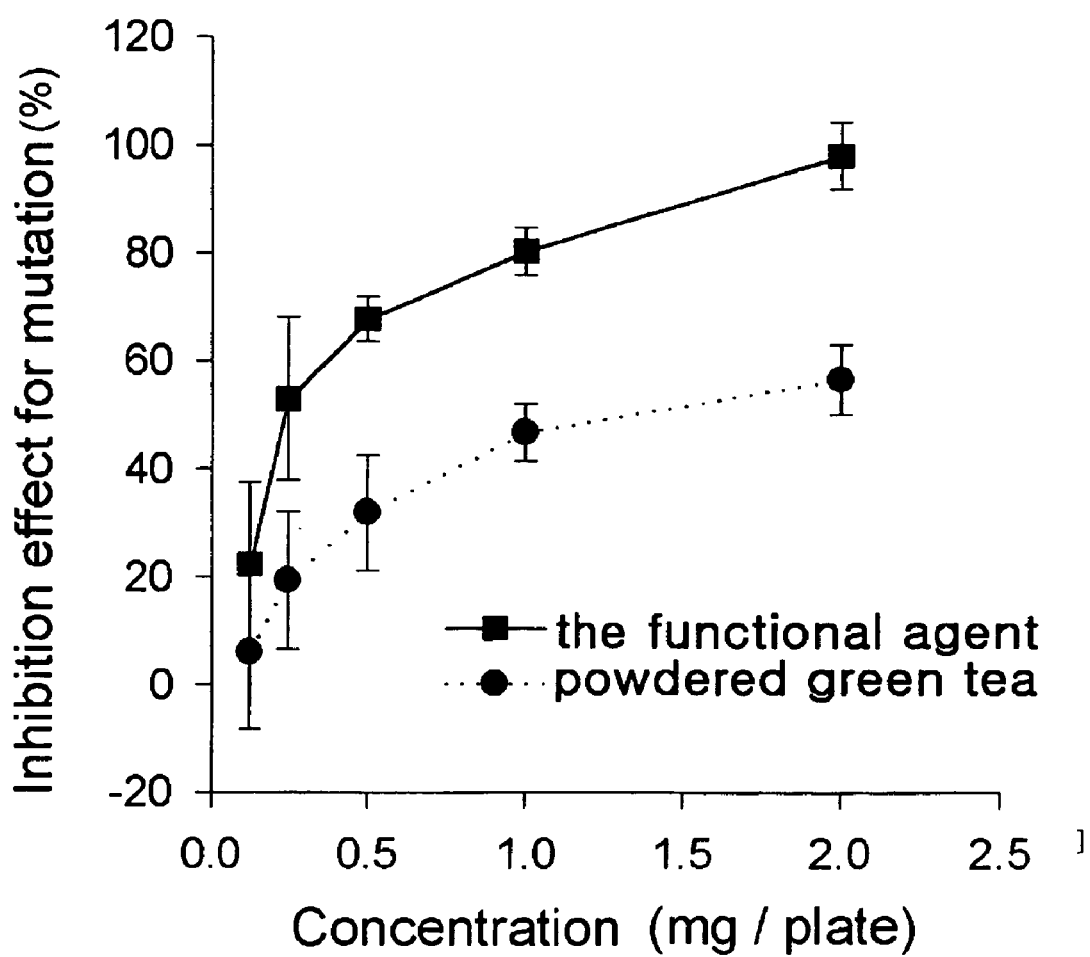
FIG. 19 is a graph showing the inhibition effect for mutagenicity caused by benzopyrene with the functional agent, quercetin, catechin and powdered green tea.
Figure 19B:
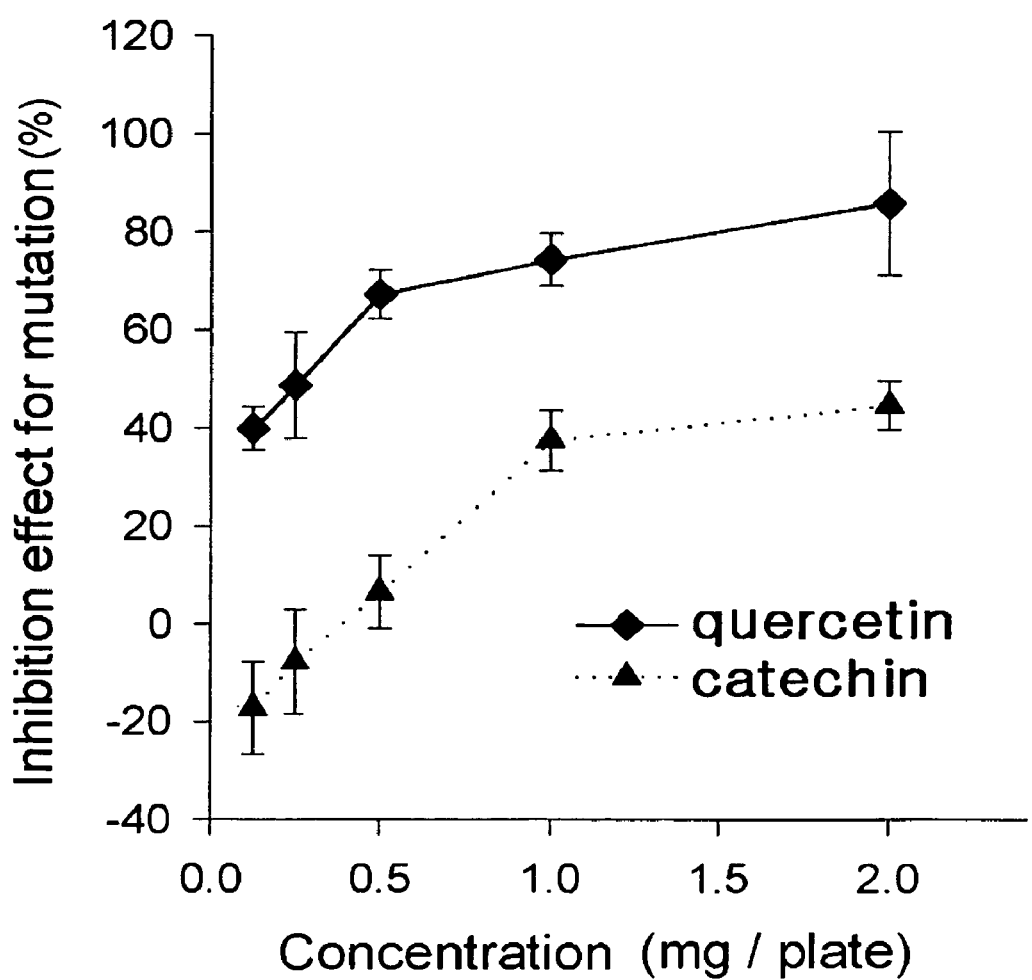

FIG. 19 is a graph showing the inhibition effect for mutation caused by benzopyrene using the functional agent of the present invention and test material. It shows the inhibition effect for mutation of *Salmonella typhimurium* TA100 by the functional agent(■), powdered green tea(●), quercetin(♦), and catechin(▲). The concentration of benzopyrene contained in each medium was 2 μg/plate. The number of spontaneously recovered mutants of *Salmonella typhimurium* TA100 which were treated with benzopyrene was 128±9. On the contrary, the functional agent of the present invention effectively inhibited the generation of mutation by benzopyrene.

EXAMPLE 10

Effect of Anti-Oxidation by the Functional Agent for Decomposing Nicotine

Although the causes of many diseases are still unclear, it has been known that toxic free radicals mediate many kinds of diseases such as arteriosclerosis (Palinski, W., Rosenfeld, M. E., Yla, H. S., Gurtner, G. C., Socher, S. S., Butler, S. W., Carew, T. E., Steinberg, D., and Witztum, J. L. (1989) *Proc. Natl. Acad. Sci.*, 86, 1372–1376), local anemia by contraction of blood vessel (Hammond, B., Kontos, H. A., and Hess, M. L. (1985) *Can. J. Physiol. Pharmacol.*, 63, 173–187), inflammation(Cheeseman, K. H., and Forni, L. G. (1988) *Biochem. Pharmacol.*, 37, 4225–4233), cancer(Weitzman, S. A., Weitberg, A. B., Clark, E. P., and Stossel, T. P. (1985) *Science*, 227, 1231–1233), and articular rheumatism (Fantone, J. C., and Ward, P. A. (1985) *Human Pathol.*, 16, 973–978). Therefore, a free radical scavenger can be expected as an effective treatment by reducing the level of free radicals. Thus, the development of a safe and effective antioxidant has been researched.

In the present test, $O_2^-$ scavenging effect of the functional agent, powdered green tea, quercetin and catechin were tested by using DPPH (1,1-diphenyl-2-picrylhydrazyl) and SOD (superoxide dismutase) kits (Wako, Japan).

DPPH was dissolved in a solvent mixing ethanol and water in a ratio of 2:1 to set concentration of $2 \times 10^{-4}$ M. The concentration of the functional agent, powdered green tea, quercetin and catechin, was made to 1/10 or less of DPPH. 1.5 ml of DPPH was placed into a cuvette and 1.5 ml of antioxidant solution was added and evenly mixed. Right after mixing, the change of absorbance (523 nm) according to time was measured and the decomposition rate was calculated.

Decomposition rate=
(initial absorbance of DPPH−absorbance after adding each specimen according to time)/
initial absorbance of DPPH×100     (Calculating formula 3)

The principle of SOD kit is when xanthine oxidase acts to xanthine, $O_2^-$ is generated. The generated $O_2^-$ reduces coexisting $NO_2^-$ TB (nitrobluetetrazolium) to show a color-forming reaction. However, superoxide dismutase(SOD) or a material removing the generated $O_2^-$ inhibits the color-forming reaction. By using this principle, it is possible to measure the inhibition effect of the generated $O_2^-$. The test method concerning $O_2^-$ scavenging effect is as follows. 0.4 mM xanthine, 0.1M phosphate buffer solution (pH 8.0) and 0.1 ml of each specimen was added into 1 ml of 0.048 unit/ml xanthine oxidase, was added. They were evenly mixed and heated at 37° C. for 20 minutes. The enzyme reaction was stopped by adding 2 ml of 69 mM SDS (sodiumdodecyl sulfate) and absorbance was measured at 560 nm. Water was used as a control. A blank test of enzyme and reagent was carried out by the same method. Table 2 shows the detail.

TABLE 2

|  | Main test | | Blank test | |
| --- | --- | --- | --- | --- |
|  |  |  | Sample blank | Reagent blank |
|  | Sample(s) | Blank (B1) | (S-B1) | (B1-B1) |
| Specimen | 0.1 ml (specimen) | 0.1 ml (distilled water) | 0.1 ml (specimen) | 0.1 ml (distilled water) |
| Color-forming solution | 1 ml | 1 ml | 1 ml | 1 ml |
| Enzyme solution | 1 ml | 1 ml | — | — |
| Blank solution | — | — | 1 ml | 1 ml |

The calculating method for the efficiency of anti oxidation is as follows.

SOD activation value(inhibition rate %)=
$(E_{B1}-E_{B1-B1})-(E_S-E_{S-B1})/$
$(E_{B1}-E_{B1-B1}) \times 100$     (Calculating formula 4)

Figure 20:
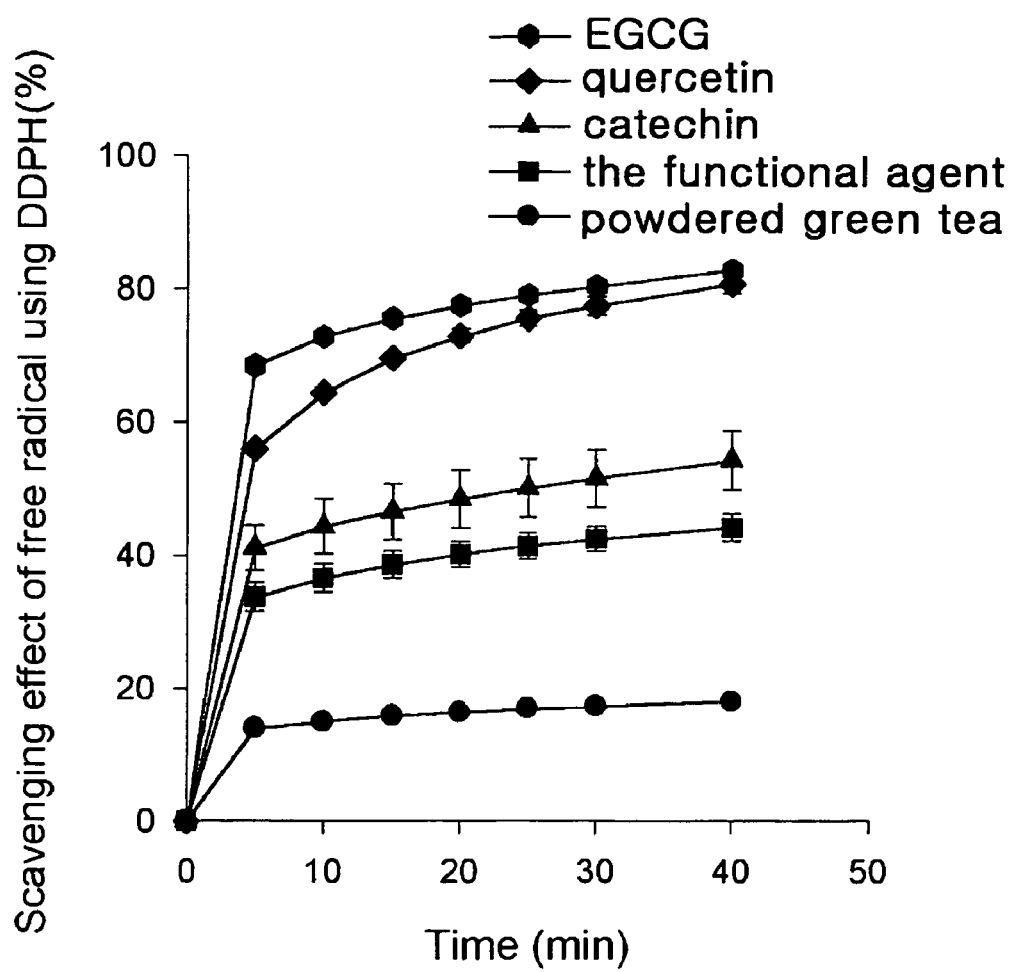
FIG. 20 is a graph showing the scavenging effect of free radicals of the functional agent, powdered green tea, quercetin and catechin.

FIG. 20 is a graph showing scavenging effect of free radicals using DPPH (1,1-diphenyl-2-picrylhydrazyl) of the functional agent, powdered green tea, quercetin and catechin. DPPH radical scavenging effect of EGCG was two times higher than that of the functional agent and catechin. However, the DPPH radical scavenging effect of the functional agent was four times higher than powdered green tea.

Figure 21:
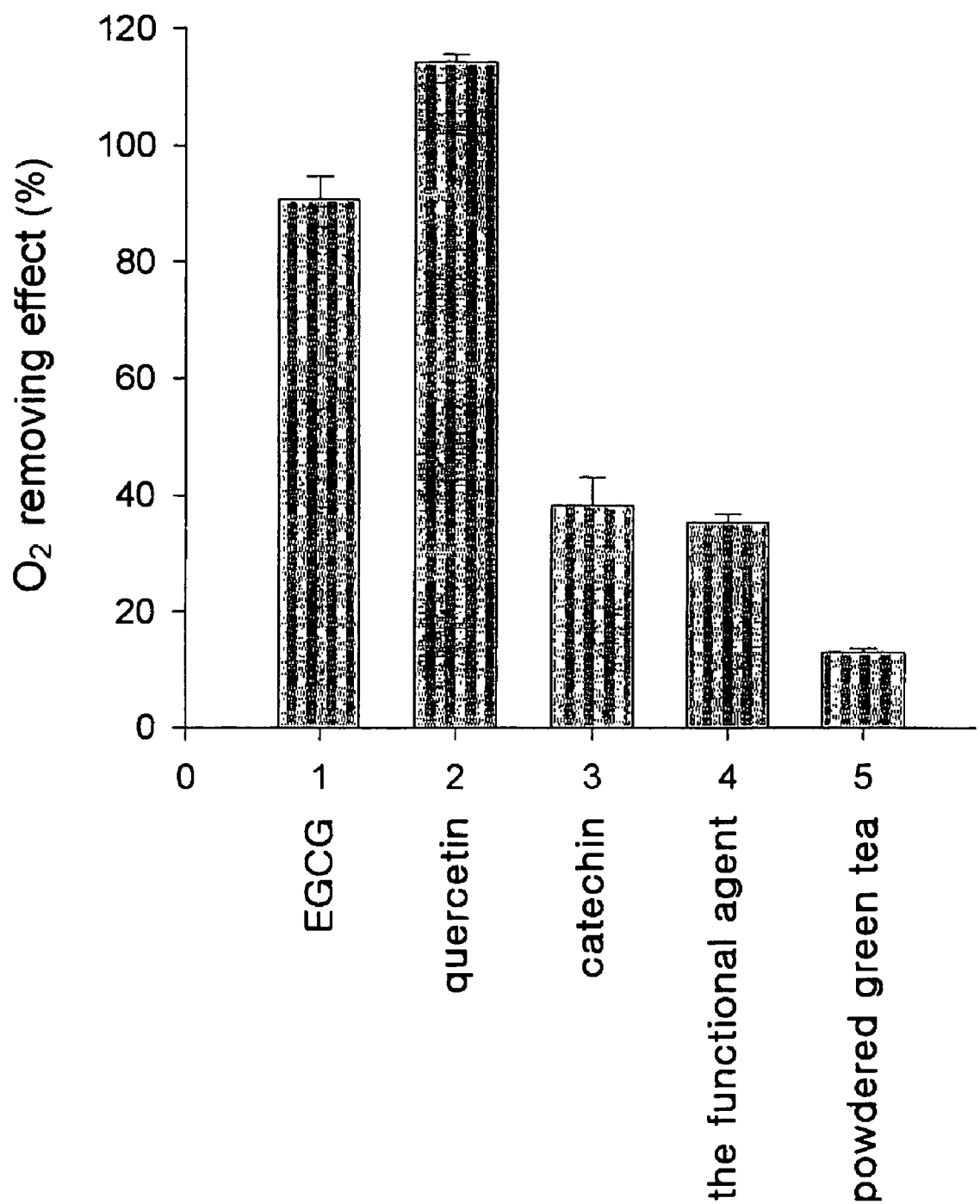
FIG. 21 is a graph showing the $O_2^-$ removing effect of the functional agent, powdered green tea, quercetin and catechin by using SOD kit.

FIG. 21 is a graph showing the result of $O_2^-$ scavenging effect of the functional agent, powdered green tea, quercetin and catechin by using SOD kit. Although quercetin showed the highest anti oxidation effect, the functional agent showed the same effect as that of purified catechin.

EXAMPLE 11

Quantification of Quercetin

Quercetin is a flavonoid uniquely discovered from photosynthetic plants. When a normal dietetic treatment is done, quercetin is assumed to be consumed about 25 mg per day.

In addition, recently quercetin was used as an anti-cancer medicine in primary clinic (Ferry, D. R., Smith, A., Malkhandi, J., Fyfe, D. W., deTakats, P. G., Anderson, D., Baker, J., Kerr, D. J. (1996) *Cancer Res.* 2(4):659–68). Many proofs have been reported that quercetin acts excellently as an anti-cancer medicine. It was reported that the propagation of cell strain such as a breast cancer (Scambia, G., Ranelletti, F. O., Benedetti, Panici, P., Piantelli, M., Bonanno, G., De Vincenzo, R., Ferrandina, G., Pierelli, L., Capelli, A., Mancuso, S. (1991) *Cancer Chemother Pharmacol.* 28(4):255–8), leukemia(Larocca, L. M., Piantelli, M., Leone, G., Sica, S., Teofili, L., Panici, P. B., Scambia, G., Mancuso, S., Capelli, A., Ranelletti, F. O. (1990) Type II oestrogen binding sites in acute lymphoid and myeloid leukaemias: growth inhibitory effect of oestrogen and flavonoids. *Br J Haematol.* 75(4):489–95), uterus cancer (Scambia, G., Ranelletti, F. O., Benedetti, Panici, P., Bonanno, G., De Vincenzo, R., Piantelli, M., Mancuso, S. (1990) Synergistic antiproliferative activity of quercetin and cisplatin on ovarian cancer cell growth. *Anticancer Drugs.* 1(1): 45–8), stomach cancer(Yoshida, M., Sakai, T., Hosokawa, N., Marui, N., Matsumoto, K., Fujioka, A., Nishino, H., Aoike, A. (1990) *FEBS Lett.* 15;260(1):10–3), and colon cancer(Agullo, G., Gamet, L., Besson, C., Demigne, C., Remesy, C. (1994) *Cancer Lett.* 25; 87(1):55–63) was inhibited in a concentration of quercetin 10 μM.

In the present test, quercetin contained in the functional agent for decomposing nicotine was quantified. In order to extract quercetin contained in the functional agent or powdered green tea, they were dissolved in extract solution of mixture of methanol and DMSO (4:1) and vigorously mixed for 30 seconds. A centrifugal separation was carried out to the mixed solution for 10 minutes at 9000 rpm and a supernatant was taken out. The supernatant and the same amount of distilled water were mixed and injected to a reverse phase column(Delta-pak C18, 300 Å, Waters510). A mobile phase was 56% of 0.1 M ammonium acetate (pH 5.15) and 44% of methanol, and flow rate was 0.3 mL/min. Absorbance was measured at 375 nm by a M720 absorbance detector (Yongin, Co. Korea).

Figure 22:
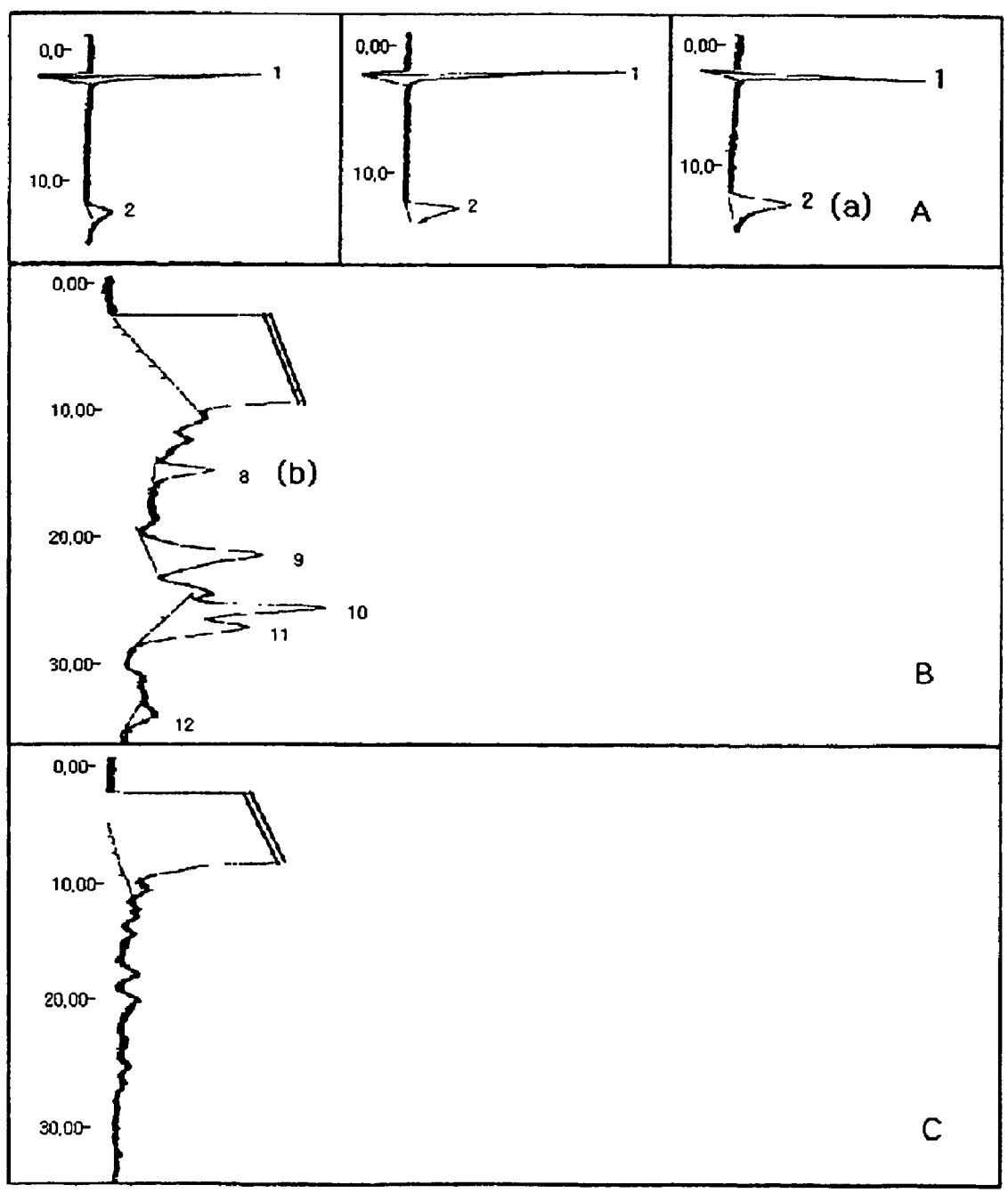
FIG. 22 is a HPLC profile showing an amount of quercetin contained in the functional agent solution.

FIG. 22 is a graph showing amount of quercetin contained in the functional agent solution for decomposing nicotine quantified by HPLC (high performance liquid chromatography). (a) of A in FIG. 22 shows a standard peak of 60, 120, 160 ng of quercetin concentration and (b) of B shows quercetin peak(numner 8) for the functional agent solution, so that the functional agent contains 56 ng/mg of quercetin. However, as seen from C of FIG. 22, quercetin peak was not detected from powdered green tea even in 5 mg.

EXAMPLE 12

Anti-Cancer Activity of the Functional Agent

NNK shows high specificity to induce lung cancer for various laboratory animals in carcinogens found in tobacco smoke (Hoffmann, D., Rivenson, A., Chung, F-L., and Hecht, S. S. (1991) *Crit. Rev. Toxicol.*, 21, 305–311; International Agency for Research on cancer. (1986) Tobacco Smoking, Vol 38. Lyon, France: IARC). Also, NNK is one of nitrosamines that have strong carcinogen found in tobacco. There have been many papers concerning the effect of green tea, especially EGCG, to inhibit generation of a lung cancer(Wang, Z. Y., Hong, J. Y., Huang, M. T., Reuhl, K. R., Conney, A. H., and Yang, C. S. (1992) *Cancer Res.* 52, 1943–1947 ; Xu, Y., Ho, C. T., Amin, S. G., Han, C., and Chung, F. L. (1992) *Cancer Res.* 52, 3875–3879; Chung, F. L., Wang, M., Rivenson, A., latropoulos, M. J., Reinhardt, J. C., Pittman, B., Ho, C. T., and Amin, S. G. (1998) *Cancer Res.* 58,4096–4101).

The A/J mice, 3 weeks old, were purchased from the SLC Inc. (Japan). The animals were maintained under specific pathogen-free conditions and housed under standardized conditions (five mice/cage; 20±5□, 50±15%, and 12 h light-dark cycles). Stock solutions of NNK were prepared in PBS (5 mg/ml). The effect of functional agent on NNK-induced tumorigenesis was studied using a model established by Xu et al. (1992).

When the A/J mice were 6 weeks old, 24 male mice were divided into the following three groups; N-group (5 animals, only water), C-group (10 animals, NNK and water treated) and T-group (9 animals, NNK and functional agent treated). In the animal test, each group was water and 0.6% functional agent as the source of drinking for the three weeks before NNK were administered. After three weeks, except N-group, other groups (C-group and T-group) were administered three times weekly for 10 weeks. The A/J mice were administered a single i.p. dose of NNK (34.95 mg/kg body weight).

After six weeks, the animals were weighed and sacrificed by carbon dioxide inhalation. The mice had access to the food and water (or functional agent) ad libitum, and the powder feeders were cleaned and replenished with fresh diet three during the bioassay. Body weights were recorded once weekly for the treatment period and then once monthly for the remainder of the bioassay.

A complete necropsy was performed on all animals and performed by Korea Research Institute of Chemical Technology (KRICT). The lungs, livers, and stomach were removed, weighed, and fixed in 10% neutral buffered formalin. Following fixation, the tissue was trimmed, embedded in paraffin, sectioned 5 μm thick and stained with hematoxylin and eosin. For the extended evaluation, lungs were sectioned serially at approximately 3 mm intervals. All sections were examined microscopically. Tumor incidence was determined by dividing the number of animals with tumor by the number of animals in each group.

An average weight of each group was measured and shown in the graph.

Figure 23:
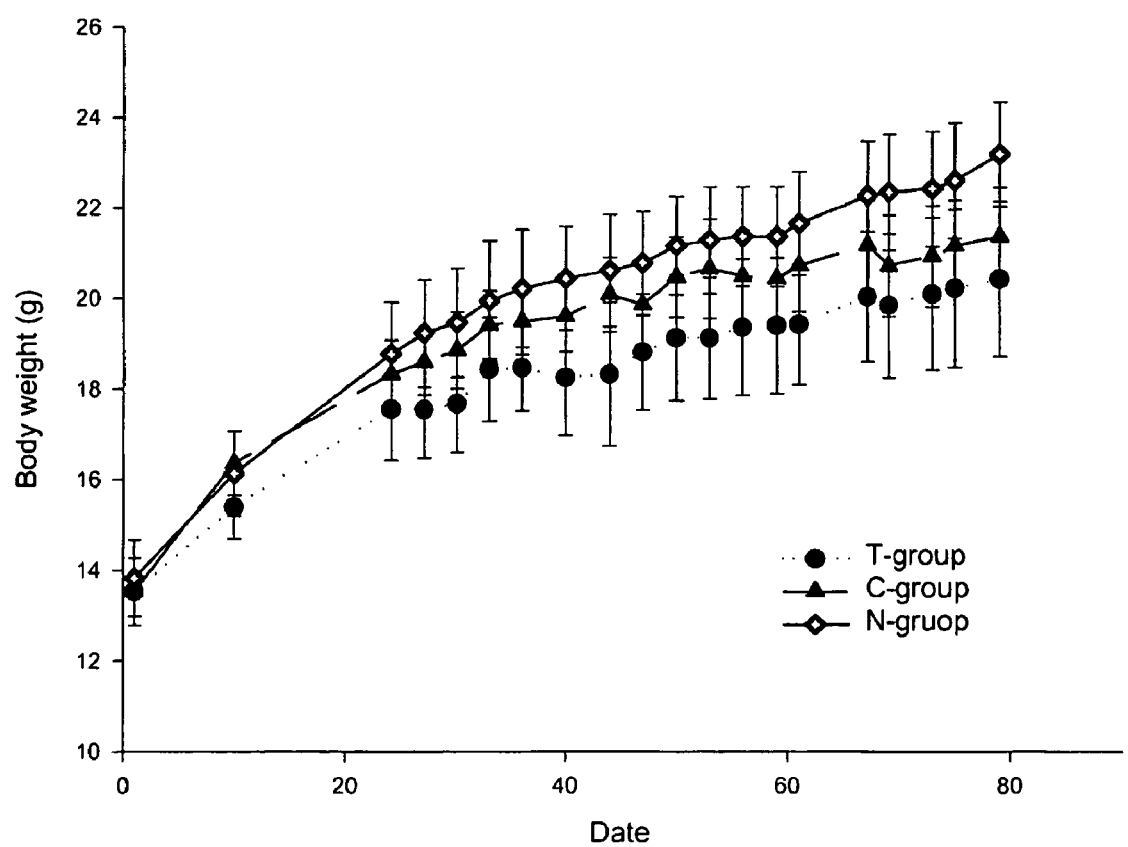
FIG. 23 is a graph showing the weight of A/J mice in test for inhibiting lung cancer induced NNK using the functional agent.

FIG. 23 is a graph showing the weight of A/J mice in each group, which indicates the inhibition effect for the generation of lung cancer induced NNK by the functional agent for decomposing nicotine.

Screening of the mouse colony indicated no viral or bacterial infection at the end of the lung tumor bioassay. At the time of sacrifice, no gross pathological change related to toxicity was observed n the livers, lung, and stomach of mice fed the NNK+functional agent. The effects of functional agent treatments on lung tumorigenesis as chemopreventive agent are shown in TABLE 3 in the experiments.

TABLE 3 shows the inhibition effect for the generation of lung cancer by the functional agent.

TABLE 3

| N-Group | 1 | 2 | 3 | 4 | 5 |
|---------|---|---|---|---|---|
| Lung    | N(15) | N(16) | N(15) | N(15) | N(15) |
| Liver   | N | N | N | N | N |
| Stomach | N | N | N | N | N |

TABLE 3-continued

| C-Group | 1 | 2 | 3 | 4 | 5 | 6 | 7 | 8 | 9 | 10 | Sum | Total |
|---|---|---|---|---|---|---|---|---|---|---|---|---|
| Lung | (14) | (14) | (14) | (15) | (14) | (16) | (15) | (13) | (14) | (15) | (144) | 144 |
| Adenoma | 0/2 | 6/5 | 2/4 | 1/3 | 5/7 | 3/9 | 1/4 | 3/4 | 6/7 | 4/4 | 31/49 | 80 |
| Hyperplasia | 2/5 | 4/4 | 1/6 | 6/7 | 2/8 | 3/6 | 5/6 | 6/6 | 3/7 | 4/9 | 36/64 | 100 |
| Liver | N | – | N | N | – | N | N | N | – | N | | |
| Microgranuloma | – | + | – | – | +++ | – | – | – | + | – | | |
| Stomach | N | N | N | N | N | N | N | N | N | N | | |
| T-Group | | 2 | 3 | 4 | 5 | 6 | 7 | 8 | 9 | 10 | Sum | Total |
| Lung | | (14) | (14) | (14) | (14) | (15) | (14) | (14) | (15) | (12) | (126) | 126 |
| Adenoma | | 1/5 | 2/5 | 2/8 | 3/4 | 4/2 | 6/1 | 0/3 | 1/2 | 3/3 | 22/23 | 55 |
| Hyperplasia | | 0/5 | 2/11 | 7/5 | 1/2 | 2/6 | 2/5 | 2/1 | 2/3 | 1/2 | 19/40 | 59 |
| Liver | | – | – | N | – | – | N | N | N | N | | |
| Microgranuloma | | – | – | – | + | +++ | – | – | – | – | | |
| Stomach | | N | N | N | N | N | N | N | N | N | | |

(N: normal, +: minimal, ++: mild, +++: moderate)

As expected, N-group mice had no incidence of spontaneous tumors. C-group were resulted in 55.6% (80/144) mice bearing bronchiolo-alveolar adenomas after 10 weeks. When 0.6% functional agent was given in drinking water (T-group), lung adenomas was significantly reduced (43.6%, 55/126). In addition, in foci of bronchiolo-alveolar hyperplasia, tumor incidences of T-group were significantly reduced from 69.4% to 46.8%. In addition, liver microgranuloma also observed at some mice of C-group (3 mice) and T-group (2 mice). The incidences of stomach tumors were not observed at two groups. This result shows the inhibitory effects of functional agent on the formation of lung tumorigenesis in NNK-treated mice. Tumor incidence of T-group corresponds to a 17% reduction of lung tumor formation in these groups as compared with the C-group.

As above, the functional agent or drink of the present invention facilitates the decomposition of nicotine and inhibits the generation of nitroso-compound that is carcinogen. In addition, the functional agent inhibits activity of cytochrome $P_{450}$ 1A2 enzyme to inhibit generation of carcinogen by NNK and shows an anti-oxidant effect as well as inhibits mutation by NNK and benzopyrene, and the generation of lung cancer.

EXAMPLE 18

Toxicity Test

1. Animals

Species and strains: Specific pathogens free Spr4aue-Dawley rats (BioGenomics Inc.)

Sprague-Dawley rats are one of the most widely used experimental animals in the toxicity testinas. Because of easy access to the basic information on rats, it might be very informative to use rats in assessing the experimental results. In addition, rats have been selected by the sponsor in order to satisfy the regulatory requirements for toxicity testing in a rodent species.

Twenty-four male rats aged 4 weeks weighing 72.2–81.3 g were used after 7 days of quarantine and acclimatization under SPF conditions. Twenty males, ranging from 105.7 to 118.7 g on the day of treatment, were used for this study. Twenty-four female rats aged 4 weeks weighing 69.1–80.3 g were used after 7 days of quarantine and acclimatization under SPF conditions. Twenty healthy females, ranging from 97.7 to 112.4 g on the day of treatment, were used for this study.

2 Housing Conditions

Environmental condition: The animal room (Room No. 2 in Animal Care Area III) was maintained at the temperature of 23±3° C., the relative humidity of 55±15%, the air ventilation of 10–20 times/hr, and the light intensity of 150–300 Lux. A 12 hr light/dark cycle was used. All personnels in animal facility wore sterilized cloths, soft caps, masks, and gloves autoclaved at 121° C. for 20 min. This experiment was conducted in facilities approved by the American Association for Accreditation of Laboratory Animal Care (AAALAC). All procedures were approved by our Institutional Animal Care and Use Committee (IACUC).

Throughout the quarantine and observation period, 5 animals were maintained in a stainless-steel wire-mesh cage (220W×41OL×200H mm).

3. Diet

Pelleted foods for experimental animals were purchased from PMJ Nutritional International Inc. gamma-ray irradiated (10.8 kGy) and given ad libitum.

The UV-irradiated municipal tap water was given ad libitum.

The water was analyzed in Daejeon Regional Institute of Health and Environment, Korea.

4. Method of Administration

Dose selection: Because the test item is being developed as a food additive, it is expected that the toxicity of this item is extremely low. Accordingly, 5000 mg/kg was selected for the highest dose as a limit test dose and then 2000 and 800 mg/kg were selected as middle and low dose, respectively, using a common ratio of 2.5. A control group was also added.

TABLE 4

| Group | Sex | No. of animals | Animal No. | Volume (ml/kg) | Dose (mg/kg) |
|---|---|---|---|---|---|
| Control | Male | 5 | 1–5 | 10 | 0 |
| | Female | 5 | 21–25 | 10 | 0 |
| T1 | Male | 5 | 6–10 | 10 | 800 |
| | Female | 5 | 26–30 | 10 | 800 |
| T2 | Male | 5 | 11–15 | 10 | 2000 |
| | Female | 5 | 31–35 | 10 | 2000 |
| T3 | Male | 5 | 16–20 | 10 | 5000 |
| | Female | 5 | 36–40 | 10 | 5000 |

Test item: The functional agent was used after dissolution in sterilized distilled water immediately before treatment and those of lower groups were prepared by stepwise dilution of that of the highest dose group. The vehicle control rats received sterilized distilled water only.

Route and treatment: The rats were fasted overnight prior to dosing and the test item was administered orally by gavage. After the test item was administered, the rats were fasted for a further 3–4 hours.

Administration: The test item was administered in a single dose by gavage to the rats with a dose volume of 10 ml/kg body weight. The application volume was calculated according to the fasted body weight on the treatment day.

5. Observation, Measurement, and Examination

Mortality and clinical observation: Clinical signs and mortality were checked every hour until 6 hour after dosing and then once a day thereafter up to day 14.

Body weight: Individual body weights of animals were measured shortly before the test item administration and on days 1, 3, 7, and 14 after the treatment thereafter.

6. Results

Mortality and Lethal dose: No animal in both sexes was found dead by treatment of the test item during the testing period. Therefore, it was estimated that the lethal doses of the test item are considered to be over 5000 mg/kg in both sexes.

Clinical signs: No clinical signs were observed in any dose groups by treatment of the test item.

Gross findings: At necropsy on day 14 after treatment, no treatment-related effects were found in any dose groups.

To evaluate the acute toxicity of the functional agent by a single oral dose, the functional agent was administered by gavage to 5 male and female Sprague-Dawley rats, respectively, at dose levels of 0, 800, 2000, and 5000 mg/kg body weight. Parameters measured during the 14-day observation period were mortality, clinical signs, body weight chanaes, and aross findings.

There were no treatment-related effects on mortality, clinical sign, body weight change and necropsy finding in Sprague-Dawley rats. In the highest dose group, the test item was administered by average at a dose level of 5000 mg/kg as a limit test dose and the results of the study showed that a single oral dose of the functional agent to rats did not cause any acute toxic effect up to 5000 mg/kg body weight.

Based on the results, it was concluded that a single oral dose of the functional agent did not cause any toxic effect in Sprague-Dawley rats at 5000 mg/kg or below, and that the minimal lethal doses were considered to be over 5000 mg/kg body weight for both sexes.

What is claimed is:

1. A functional agent for decomposing nicotine prepared by drying a composition comprising:
    (a) powder of green tea leaves;
    (b) mulberry extract prepared by steeping mulberry leaves in water;
    (c) apple juice prepared by squeezing apples;
    (d) licorice root extract prepared by steeping in water;
    (e) orange peel extract prepared by steeping in water;
    (f) ginkgo nut extract prepared by squeezing ginkgo nut;
    (g) celery extract prepared by squeezing celery; and
    (h) lemon extract prepared by squeezing lemon, and
    wherein the ratio of parts by weight of powder of green tea leaves is 50 to 500, the ratio of parts by weight of mulberry leaves is 7.5 to 75, the ratio of parts by weight of apple is 3 to 30, the ratio of parts by weight of licorice root is 3 to 30, the ratio of parts by weight of orange peel is 1.5 to 15, the ratio of parts by weight of ginkgo nut is 7.5 to 75, the ratio of parts by weight of celery is 3 to 30, and the ratio of parts by weight of lemon is 3 to 30.

2. The functional agent for decomposing nicotine of claim 1, wherein the agent is used as food, food additives, medicines, drinks, or drink additives.

3. The functional agent for decomposing nicotine of claim 1 wherein the agent is packaged and in capsule form.

4. A functional drink for decomposing nicotine comprising 0.1 to 5% by weight of the functional agent of claim 1 with water.

5. A method of preparing a functional agent for decomposing nicotine comprising:
    (a) preparing filtrates by squeezing and filtering ginkgo nut, celery, apple, and lemon;
    (b) preparing extracts by steeping licorice root and dried orange peel in water, adding mulberry leaves to steep and filtering; and
    (c) mixing the filtrates of (a), extracts of (b), and powder of green tea leaves, then filtering and spray-drying the mixture; and
    wherein the ratio of parts by weight of powder of green tea leaves is 50 to 500, the ratio of parts by weight of mulberry leaves is 7.5 to 75, the ratio of parts by weight of apple is 3 to 30, the ratio of parts by weight of licorice root is 3 to 30, the ratio of parts by weight of orange peel is 1.5 to 15, the ratio of parts by weight of ginkgo nut is 7.5 to 75, the ratio of parts by weight of celery is 3 to 30, and the ratio of parts by weight of lemon is 3 to 30.

* * * * *